US010106619B2

(12) United States Patent
Croft et al.

(10) Patent No.: US 10,106,619 B2
(45) Date of Patent: Oct. 23, 2018

(54) VIRUS VACCINATION AND TREATMENT METHODS WITH OX40 AGONIST COMPOSITIONS

(75) Inventors: Michael Croft, San Diego, CA (US); Shahram Salek-Ardakani, San Diego, CA (US); Magdalini Moutaftsi, Del Mar, CA (US); Alessandro Sette, La Jolla, CA (US); Carl F. Ware, Solana Beach, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 1246 days.

(21) Appl. No.: 11/867,621

(22) Filed: Oct. 4, 2007

(65) Prior Publication Data

US 2012/0141465 A1   Jun. 7, 2012

Related U.S. Application Data

(60) Provisional application No. 60/849,514, filed on Oct. 4, 2006.

(51) Int. Cl.
*C07K 16/28* (2006.01)
*A61K 39/00* (2006.01)
*A61K 39/12* (2006.01)

(52) U.S. Cl.
CPC .......... *C07K 16/2878* (2013.01); *A61K 39/12* (2013.01); *A61K 2039/505* (2013.01); *A61K 2039/5254* (2013.01); *A61K 2039/55516* (2013.01); *C07K 2317/75* (2013.01); *C12N 2710/24134* (2013.01)

(58) Field of Classification Search
None
See application file for complete search history.

(56) References Cited

U.S. PATENT DOCUMENTS

| | | | |
|---|---|---|---|
| 6,566,082 B1 | 5/2003 | Weinberg et al. | 435/7.24 |
| 2002/0054873 A1 | 5/2002 | Weinberg | 424/141.1 |
| 2004/0247563 A1* | 12/2004 | Lynch et al. | 424/85.2 |
| 2006/0062800 A1* | 3/2006 | Cohen et al. | 424/186.1 |
| 2007/0207159 A1 | 9/2007 | Weinberg | 424/159.1 |
| 2009/0269365 A1* | 10/2009 | Koelle et al. | 424/186.1 |

FOREIGN PATENT DOCUMENTS

WO   03/106498   12/2003

OTHER PUBLICATIONS

Bansal-Pakala, Pratima, et al., Costimulation of CD8 T Cell Responses by OX-401, The Journal of Immunology, 2004, 172:4821-4825.
Salek-Ardakani, Shahram, et al., OX40 Drives Protective Vaccinia Virus-Specific CD8 T Cells1,2, The Journal of Immunology, 2008, 181:7969-7976.
Salek-Ardakani, Shahram, et al., Targeting OX40 Promotes Lung-Resident Memory CD8 T Cell Populations That Protect against Respiratory Poxvirus Infection, Journal of Virology, 2011, 85(17):9051-9059.
Salek-Ardakani, Shahram, et al., The TNFR Family Members OX40 and CD27 Link Viral Virulence to Protective T Cell Vaccines in Mice, The Journal of Clinical Investigation, 2011, 121(1):296-307.
Humphreys, I.R., et al., Cytomegalovirus Exploits IL-10-Mediated Immune Regulation in the Salivary Glands, JEM, 2007, 204:(5):1217-1225.
Humphreys, I.R., et al., OX40 Costimulation Promotes Persistence of Cytomegalovirus-Specific CD8 T Cells: A CD4-Dependent Mechanism, J. Immunol, 2007, 179:2195-2202.
Lee, S.W., et al., Functional Dichotomy Between OX40 and 4-1BB in Modulating Effector CD8 T Cell Responses, J. Immunol., 2006, 177:4464-4472.
Song, A.X., et al., OX40 and Bcl-x(subscript)1 Promote the Persistence of CD8 T Cells to Recall Tumor-Associated Antigen, J. Immunol., 2005, 175:3534-3541.
Oserhoff, C., et al., Dissociation Between Epitope Hierarchy and Immunoprevelance in CD8 Responses to Vaccinia Virus Western Reserve, The Journal of Immunology, 2008, 180:7193-7202.
Moutaftsi et al., Correlates of Protection Efficacy Induced by Vaccinia Virus-Specific CD81 T-Cell Epitopes in the Murine Intranasal Challenge Model, European J. Immunol; 2009; pp. 712-722.
Salek-Ardakani et al.; The TNFR Family Members OX40 and CD27 Link Viral Virulence to Protective T Cell Vaccines in Mice; The Journal of Clinical Investigation, vol. 121, No. 1, Jan. 2011; 12 pages.
Salek-Ardakani et al.; Targeting OX40 Promotes Lung-Resident Memory CD8 T Cell Populations That Protect Against Respiratory Poxvirus Infection; J. Virol; vol. 85; No. 17; Sep. 2011; pp. 9051-9059.
Song, A., et al., Cooperation between CD4 and CD8 T cells for anti-tumor activity is enhanced by OX40 signals, Eur. J. Immunol. 2007, 37:1224-1232.

* cited by examiner

*Primary Examiner* — Bong-Sook Baek
(74) *Attorney, Agent, or Firm* — Pillsbury Winthrop Shaw Pittmann LLP

(57) ABSTRACT

The invention relates to compositions and methods that employ OX40 (CD134), a TNFR superfamily protein, agonists. The invention includes among other things administering an OX40 agonist alone or in combination with a viral antigen, or live or attenuated virus, to treat a viral infection, or for vaccination or immunization.

16 Claims, 8 Drawing Sheets

Specification includes a Sequence Listing.

a)

b)

c)

a)

b)

c)

VIRUS VACCINATION AND TREATMENT METHODS WITH OX40 AGONIST COMPOSITIONS

RELATED APPLICATIONS

This application claims priority to U.S. provisional application Ser. No. 60/849,514, filed Oct. 4, 2006, which is expressly incorporated herein by reference.

GOVERNMENT SUPPORT

This invention was made with government support under Grant AI67341 awarded by the National Institutes of Health. The government has certain rights in the invention.

TECHNICAL FIELD

The invention relates to vaccinating or immunizing against viral infections, by administering an OX40 agonist in combination, or in series or sequentially, with a viral antigen, or live or attenuated virus. The invention relates to treatment of viral infections by administering an OX40 agonist.

INTRODUCTION

Smallpox (variola) represented a significant threat for many years until its eradication following vaccination with Dryvax, a preparation of vaccinia virus that provided long-lasting protection against variola infection. However, vaccination was terminated a number of years ago and currently less than 50 percent of the world's population have been exposed to variola or vaccinia. In light of current issues with bioterrorism, many people in the world are potentially at risk if this fatal virus reenters circulation. Immunization with vaccinia is the only option for protecting against smallpox, but diluting the current supply of vaccine 1/10 to 1/100 strongly reduces its effectiveness, suggesting other strategies for immunization or augmenting the efficacy of the current vaccine are desirable.

The death of T cell-deficient children and HIV-infected adults after vaccination, and studies of responses in vaccinated individuals, has shown that T cells especially CD8 cells, but also CD4 cells, are critical to immunity against vaccinia and variola. Although VV-specific CD8 and CD4 T cells play a role in controlling primary infection or in protection from subsequent challenge, there is little information available on the molecules that might be essential to generate and sustain a protective anti-viral CD8 or CD4 T cell response. Recent studies with LCMV have identified a direct role for type-I interferons (IFN-I) in survival of CD8 T cells. However, whether IFN-I serves as the most dominantly available survival factor for all anti-viral T cells is unclear.

SUMMARY

OX40 (also referred to as CD134, TNFRSF4 and ACT35) is a 50 kilodalton (KDa) glycoprotein and a member of the tumor necrosis factor receptor superfamily (TNFRSF) that is expressed on immune cells, particularly CD4 and CD8 T cells. The ligand for OX40, OX40L (also referred to as TXGP1L, TNFSF4, CD252), has been reported to be expressed on endothelial cells, activated antigen presenting cells including macrophages, dendritic cells, B cells and natural killer cells. Although not wishing to be bound by theory, binding between CD40 on antigen presenting cells increases OX40L expression as can lipopolysaccharide (LPS). Expression of OX40 on T cells can be induced following signaling via the T cell antigen receptor. For example, OX40 is expressed on recently activated T cells at the site of inflammation. CD4 and CD8 T cells can upregulate OX40 under inflammatory conditions. OX40 can promote a number of activities in T cells including causing their division, survival, and promoting their effector function (e.g. to kill virally infected cells). Agonist reagents (antibodies, fusion proteins, other modalities that cross-link OX40 and promote intracellular signaling) can be used to stimulate OX40 and enhance T cell immunity.

Analysis of OX40 for anti-vaccinia activity in mice against whole vaccinia virus (VV) or with specific peptide epitopes of vaccinia recognized by CD8 or CD4 T cells revealed that accumulation of VV-specific CD8 T cells over time is largely independent of IFN-1 signaling, and OX40 is critical for the magnitude of primary anti-VV specific CD8 and CD4 T cell responses, including expansion and anti-viral cytokine production, and the generation of memory cells to both dominant and subdominant VV epitopes. Anti-OX40 agonistic antibody added only during priming dramatically increased the number of VV-specific CD8 and CD4 T cells and completely protected mice against lethal VV challenge after immunization with a single CD8 T cell peptide epitope or a single CD4 T cell peptide epitope of vaccinia. Targeting OX40, a TNFR superfamily protein, expressed on both CD4 and CD8 T cells, effectively stimulates the T cell response to vaccinia virus. Stimulation of OX40 with agonist reagents can therefore be used with individual vaccinia virus peptides to promote protection against lethal challenge with the virus. Furthermore, agonist OX40 reagents can stimulate immunity and suppress replication of other viruses, including cytomegalovirus (CMV). Agonist OX40 reagents can therefore provide or augment immunity to viruses in people vaccinated or immunized with peptide or virus preparations against viral infections.

In accordance with the invention, there are provided methods of vaccinating or immunizing a subject against a viral infection. In one embodiment, a method includes administering to a subject a viral antigen, or live or attenuated virus, and an amount of an OX40 (CD134) agonist sufficient to vaccinate or immunize the subject against the viral infection.

In accordance with the invention, there are also provided methods of treating a subject for a viral infection (chronic or acute). In one embodiment, a method includes administering to a subject an amount of an OX40 (CD134) agonist sufficient to treat the subject for the viral infection (chronic or acute). In another embodiment, a method includes administering to a subject an amount of an OX40 (CD134) agonist and a viral antigen, or live or attenuated virus, sufficient to treat the subject for the viral infection (chronic or acute).

OX40 agonists include agonists binds to OX40 (CD134), such as OX40 extracellular domain. OX40 agonists include small molecules, polypeptides, such as antibody (monoclonal or polyclonal) or OX40 binding antibody subsequence or fragment (e.g., Fab, Fab', F(ab')$_2$, Fv, Fd, single-chain Fv (scFv), disulfide linked Fv, light chain variable (VL) or heavy chain variable (VH) region sequences), and OX40 ligand (OX40L) or soluble OX40 ligand (OX40L). Antibodies include mammalian, primatized, humanized and fully human antibody. Specific non-limiting examples of OX40 antibody include 112F32, 112V8, 112Y55, 112Y131, 112Z5, mAb 315, mAb131, mAb 2G2, IF7, ACT35, mAb L106 and mAb OX86. Additional specific non-limiting examples of OX40 antibody include an antibody having substantially the same binding affinity as an antibody selected from 112F32, 112V8, 112Y55, 112Y131, and 112Z5, mAb 315, mAb131, mAb 2G2, IF7, ACT35, mAb L106, and mAb OX86. Further specific non-limiting examples of OX40 antibody include an antibody that competitively inhibits binding of an antibody selected from 112F32, 112V8, 112Y55, 112Y131, and 112Z5, mAb 315, mAb131, mAb 2G2, IF7, ACT35, mAb L106, and mAb OX86.

Exemplary agonists include molecules that stimulate or increase OX40 signaling or expression. Exemplary agonists also include molecules that increase or stimulate CD4 or CD8 T cell priming.

Viral antigen, live or attenuated virus useful in accordance with the invention can be from any virus. Particular non-limiting types of viral antigens, live or attenuated virus include poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or a retrovirus.

Poxvirus viral antigen, live or attenuated virus include vaccinia virus (e.g., B8R, L4R, H3L, E9L, F15L, J4R, I1L, A3L, A8R, A23R and B2R antigens), *Molluscum contagiosum*, variola major or variola minor smallpox virus, cow pox, camel pox, sheep pox, or monkey pox antigen.

Herpesvirus viral antigen, live or attenuated virus include an alpha-herpesvirus, beta-herpesvirus, gamma-herpesvirus, Epstein Bar Virus (EBV), Cytomegalovirus (CMV), varicella zoster virus (VZV/HHV-3), or human herpes virus 1, 2, 4, 5, 6, 7, or 8 (HHV-8, Kaposi's sarcoma-associated virus) antigen.

Hepatitis viral antigen, live or attenuated virus include a hepatitis A, B, C, D, E or G antigen.

Immunodeficiency viral antigen, or attenuated virus include a human immunodeficiency virus (HIV) antigen. Non-limiting examples of HIV viral antigen, or attenuated virus include HIV-1, HIV-2 or HIV-3 antigen.

Flavivirus viral antigen, live or attenuated virus include a Yellow Fever virus, Dengue virus, Japanese Encephalitis or West Nile virus antigen.

Papilloma viral antigen, live or attenuated virus include a human papilloma virus (HPV) antigen. Non-limiting examples of human papilloma viral antigen, live or attenuated virus include a HPV strain 1, 6, 11, 16, 18, 30, 31, 42, 43, 44, 45, 51, 52, or 54 antigen.

Polyoma viral antigen, live or attenuated virus include a BK virus (BKV) or JC virus (JCV) antigen.

Rhabdovirus viral antigen, live or attenuated virus include a rabies virus or vesiculovirus antigen.

Myxovirus viral antigen, live or attenuated virus include a paramyxovirus or orthomyoxovirus antigen. Non-limiting examples of aramyxovirus a viral antigen, live or attenuated virus include a measles, mumps, pneumovirus or respiratory syncytial virus (RSV) antigen. Non-limiting examples of orthomyoxovirus viral antigen, live or attenuated virus include an influenza virus antigen.

Influenza virus viral antigen, live or attenuated virus include a influenza A, influenza B or influenza C antigen.

Arenavirus viral antigen, live or attenuated virus include a lymphocytic choriomeningitis virus (LCMV), Junin virus, Lassa virus, Guanarito virus, Sabia virus or Machupo virus antigen.

Coronavirus viral antigen, live or attenuated virus include an antigen of a virus that causes a common cold or severe acute respiratory syndrome (SARS).

Reovirus viral antigen, live or attenuated virus include a rotavirus, cypovirus or orbivirus antigen.

Picornavirus viral antigen, live or attenuated virus include a rhinovirus, apthovirus, hepatovirus, enterovirus or cardiovirus antigen.

Togavirus viral antigen, live or attenuated virus include alphavirus, sindbus virus, or rubellavirus antigen.

Bunyavirus viral antigen, live or attenuated virus include a hantavirus, phlebovirus or nairovirus antigen.

Retrovirus viral antigen, live or attenuated virus include an alpha, beta, delta, gamma, epsilon, lentivirus, spumavirus or human T-cell leukemia virus antigen. Non-limiting examples of lentivirus viral antigen, live or attenuated virus include an immunodeficiency virus antigen. Non-limiting examples of immunodeficiency viral antigen, live or attenuated virus include a bovine, porcine, equine, canine, feline or primate virus antigen. Non-limiting examples of human T-cell leukemia viral antigen, live or attenuated virus include a human T-cell leukemia virus 1 or 2 (HTLV-1 and HTLV-2) antigen.

Viruses treated, vaccinated or immunized against include any virus which may respond to an OX40 agonist. In various embodiments, a virus includes poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or retrovirus.

Poxviruses include a vaccinia virus, *Molluscum contagiosum*, variola major smallpox virus, variola minor smallpox virus, cow pox, camel pox, sheep pox, and monkey pox. Herpesviruses include alpha-herpesvirus, beta-herpesvirus, gamma-herpesvirus, Epstein Bar Virus (EBV), Cytomegalovirus (CMV), varicella zoster virus (VZV/HHV-3), and human herpes virus 1, 2, 4, 5, 6, 7, and 8 (HHV-8, Kaposi's sarcoma-associated virus). Hepatitis viruses include hepatitis A, B, C, D, E and G. Immunodeficiency viruses include human immunodeficiency virus (HIV), such as HIV-1, HIV-2 and HIV-3. Flaviviruses include Yellow Fever virus, Dengue virus, Japanese Encephalitis and West Nile viruses. Papilloma viruses include human papilloma virus (HPV), such as HPV strain 1, 6, 11, 16, 18, 30, 31, 42, 43, 44, 45, 51, 52, and 54. Polyoma viruses include BK virus (BKV) and JC virus (JCV). Rhabdoviruses include rabies virus and vesiculovirus. Myxoviruses include paramyxovirus (e.g., measles, mumps, pneumovirus and respiratory syncytial virus (RSV) and orthomyoxovirus (e.g., influenza virus, such as influenza A, influenza B and influenza C). Arenaviruses include lymphocytic choriomeningitis virus (LCMV), Junin virus, Lassa virus, Guanarito virus, Sabia virus and Machupo virus. Coronaviruses include virus that causes a common cold or severe acute respiratory syndrome (SARS). Adenoviruses include viral infections of the bronchii, lung, stomach, intestine (gastroenteritis), eye (conjunctivitis), bladder (cystitis) and skin. Reoviruses include a rotavirus, cypovirus and orbivirus. Picornaviruses include rhinovirus (e.g., causing a common cold), apthovirus, hepatovirus, enterovirus and cardiovirus. Togaviruses include alphavirus, sindbus virus, and rubellavirus. Bunyaviruses include hantavirus, phlebovirus and nairovirus. Retroviruses include alpha, beta, delta, gamma, epsilon, lentivirus, spumavirus and human T-cell leukemia virus, such as human T-cell leukemia virus 1 and 2 (HTLV-1 and HTLV-2). Lentiviruses include immunodeficiency virus, such as bovine, porcine, equine, canine, feline and primate virus.

Methods of the invention include those that provide a benefit or therapeutic effect to a subject. In various embodiments, a method protects against virus infection or pathology, reduces susceptibility to virus infection or pathology, or reduces virus titer, reduces virus proliferation, reduces the amount of a virus protein or reduces the amount of a virus nucleic acid. In additional embodiments, a method increases or stimulates virus clearance, reduces or inhibits virus infection, reduces or inhibits increases in virus titer, reduces or inhibits virus proliferation, reduces or inhibits synthesis of a viral protein or a viral nucleic acid, or reduces or inhibits virus reactivation from latency (e.g., herpesvirus reactivation from latency). In further embodiments, a method prevents, reduces or improves one or more physiological conditions, disorders, illness, diseases or symptoms caused by or associated with virus infection, reactivation or pathology. In yet additional embodiments, a method prevents, reduces or ameliorates an adverse complication associated with virus infection, reactivation or pathology.

Methods of the invention include administering the OX40 agonist at a various times. In particular embodiments, OX40 (CD134) agonist is administered prior to, substantially contemporaneously with or following vaccination or immunization of the subject against the virus. In other embodiments, OX40 (CD134) agonist is administered prior to, substantially contemporaneously with or following exposure to or infection of the subject with virus. In additional embodiments, OX40 (CD134) agonist is administered prior to, substantially contemporaneously with or following virus infection or reactivation from latency.

Methods of the invention also include increasing numbers or activation of an immune cell in a subject with or at risk of a viral infection. In one embodiment, a method includes administering to a subject an amount of OX40 (CD134) agonist sufficient to increase numbers or activation of the immune cell in the subject. In particular aspects, the immune cell is a T cell, dendritic cell (DC), CD4+ or a CD8+ cell.

Methods of the invention further include increasing or inducing an antiviral CD8+ or CD4+ T cell response in a subject with or at risk of a viral infection. In one embodiment, a method includes administering to a subject an amount of OX40 (CD134) agonist sufficient to increase or induce an antiviral CD8+ or CD4+ T cell response in the subject.

In methods embodiments, a viral antigen, or live or attenuated virus is administered prior to, substantially contemporaneously with or following administration of OX40 (CD134) agonist to the subject. In methods embodiments, a plurality of OX40 (CD134) agonists are administered to a subject, one or more times.

The invention also provides kits that include an OX40 agonist, and optionally a viral antigen, live or attenuated virus, and optionally instructions for vaccinating or immunizing a subject against a viral infection, or treating a subject having or at risk of having a viral infection, reactivation or pathogenesis. Exemplary non-limiting OX40 agonists for inclusion in kits include polypeptide, such as an antibody (polyclonal or monoclonal) or an OX40 binding subsequence or fragment thereof, OX40L and soluble OX40L. Antibody and OX40 binding subsequences and fragments can be selected from mammalian, primatized, humanized and fully human antibody. Exemplary antibody and OX40 binding subsequences and fragments are selected from 112F32, 112V8, 112Y55, 112Y131, and 112Z5, mAb 315, mAb131, mAb 2G2, IF7, ACT35, mAb L106, and mAb OX86; antibody having substantially the same binding affinity as an antibody selected from 112F32, 112V8, 112Y55, 112Y131, and 112Z5, mAb 315, mAb131, mAb 2G2, IF7, ACT35, mAb L106, and mAb OX86; and antibody that competitively inhibits binding of an antibody selected from 112F32, 112V8, 112Y55, 112Y131, and 112Z5, mAb 315, mAb131, mAb 2G2, IF7, ACT35, mAb L106, and mAb OX86. Exemplary kits can be for poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or retrovirus vaccination, immunization or treatment of viral infection.

(Left panel) Body weight was monitored after intranasal challenge with VVwr. (Right panel) Survival curves after intranasal challenge with VVwr.

Figure 7:
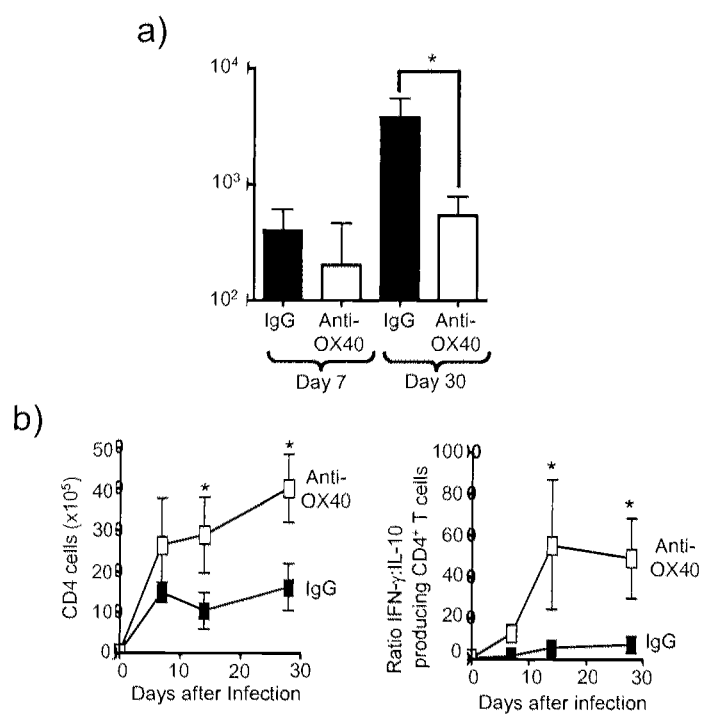

FIGS. 7A-7B show data indicating OX40 activation inhibits MCMV (murine cytomegalovirus) replication and enhances generation of protective T cells. A) MCMV-infected mice treated with IgG (closed bars) or anti-OX40 (open bars) and assayed for infectious virus. B), left) Numbers of CD4 T cells in salivary glands of IgG and anti-OX40 treated mice 0, 7, 14 and 30 days post-infection. B), right) IFNγ and IL-10 expression measured in salivary gland-derived CD4 T cells following ex-vivo stimulation with anti-CD3 and anti-CD28. Ratio of IFNγ:IL-10 producing CD4 cells, calculated as the ratio of the percentages of IFNγ expressing CD4 cells to IL-10 expressing CD4 cells.

DETAILED DESCRIPTION

The invention is based at least in part on the role of OX40 (CD134), a TNFR superfamily protein expressed on both CD4 and CD8 T cells, in anti-viral T cell responses, including T cell expansion and anti-viral cytokine production, and the generation of memory cells. In particular, anti-OX40 agonist antibody administered during antigen priming dramatically increased the number of vaccinia virus-specific CD8 and CD4 T cells and completely protected mice against a lethal vaccinia virus challenge after immunization with a single CD8 or single CD4 T cell peptide epitope of vaccinia. Agonist OX40 reagents can therefore provide or augment immunity to smallpox in people vaccinated or immunized with peptide or virus preparations against smallpox infection. More broadly, stimulation of OX40 with agonist reagents in combination compositions and methods can be used with vaccinia virus or other viral antigens to provide protection against vaccinia virus and other viruses in the context of vaccination/immunization, and in the context of treatment of a chronic or acute viral infection.

In accordance with the invention, there are provided methods of vaccinating or immunizing a subject against a viral infection. In one embodiment, a method includes administering to a subject a viral antigen, or live or attenuated virus, and an amount of an OX40 (CD134) agonist sufficient to vaccinate or immunize the subject against the viral infection.

In accordance with the invention, there are also provided methods of treating a subject for a viral infection. In one embodiment, a method includes administering to a subject an amount of an OX40 (CD134) agonist sufficient to treat the subject or the viral infection. In another embodiment, a method includes administering to a subject an amount of an OX40 (CD134) agonist and a viral antigen, or live or attenuated virus, sufficient to treat the subject or the viral infection.

OX40 agonists bind to OX40 present on one or more cells in vivo, in vitro, in primary cell isolates, passaged cells, cultured cells and immortalized cells and ex vivo. Specific non-limiting cell types that can express OX40 include activated and other T cells (e.g., activated, effector, memory or regulatory T cells) and non-T cells. Examples of non-T cells include natural killer (NK) cells, granulocytes (neutrophils), monocytes and B cells. Cells that do not naturally express OX40 can be made to express OX40, for example, by transfecting or transforming cells with an OX40 encoding nucleic acid. OX40 agonists can bind to one or more transfected or transformed cells that express or produce OX40.

OX40 agonists detectably induce, increase, promote, stimulate or enhance an activity or function of OX40. Thus, an OX40 agonist detectably induces, increases, promotes, stimulates or enhances one or more OX40 activities or functions, which can include, for example, binding of OX40 to OX40 ligand (OX40L), OX40 mediated signaling or expression, or an OX40-mediated or OX40-modulatable cell response, or another OX40 activity or function as set forth herein or otherwise one that one skilled in the art would know.

OX40 agonists include molecules that bind to an OX40 amino acid sequence. OX40 amino acid sequences include mammalian (e.g., primate, human) forms of OX40. A non-limiting example of OX40 is a full length human sequence set forth as:

```
                                         SEQ ID NO: 13
MCVGARRLGRGPCAALLLLGLGLSTVTGLHCVGDTYPSNDRCCHECRPG

NGMVSRCSRSQNTVCRPCGPGFYNDVVSSKPCKPCTWCNLRSGSERKQL

CTATQDTVCRCRAGTQPLDSYKPGVDCAPCPPGHFSPGDNQACKPWTNC

TLAGKHTLQPASNSSDAICEDRDPPATQPQETQGPPARPITVQPTEAWP

RTSQGPSTRPVEVPGGRAVAAILGLGLVLGLLGPLAILLALYLLRRDQR

LPPDAHKPPGGGSFRTPIQEEQADAHSTLAKI,.
```

OX40 agonists include molecules that bind to an amino acid sequence within or comprising OX40 extracellular domain. A non-limiting example OX40 extracellular domain is a sequence set forth as: MCVGARRLGR GPCAALLLLG LGLSTVTGLH CVGDTYPSND RCCHECRPGN GMVSRCSRSQ NTVCRPCGPG FYNDVVSSKP CKPCTWCNLR SGSERKQLCT ATQDTVCRCR AGTQPLDSYK PGVDCAPCPP GHFSPGDNQA CKPWTNCTLA GKHTLQPASN SSDAICEDRD PPATQPQETQ GPPARPITVQ PTEAWPRTSQ GPS, SEQ ID NO:14.

OX40 agonists include OX40L and functional subsequences of OX40L that bind to OX40. One non-limiting example of a full length human OX40L is a sequence set forth as:

```
                                         SEQ ID NO: 15
    MERVQPLEEN VGNAARPRFE RNKLLLVASV IQGLGLLLCF

TYICLHFSAL QVSHRYPRIQ SIKVQFTEYK KEKGFILTSQ

KEDEIMKVQN NSVIINCDGF YLISLKGYFS QEVNISLHYQ

KDEEPLFQLK KVRSVNSLMV ASLTYKDKVY LNVTTDNTSL

DDFHVNGGEL ILIHQNPGEF CVL,.
```

The term "agonist" and grammatical variations thereof used in reference to an OX40 reagent, means a molecule that directly or indirectly induces, increases, promotes, stimulates or enhances an activity or function of OX40. An OX40 agonist may directly interact with OX40, for example, by binding to or associating with OX40. An OX40 agonist may indirectly interact with OX40, for example, by acting through an intermediary, for example, the agonist binds to or modulates a molecule that in turn binds to or modulates OX40. An OX40 agonist may also directly or indirectly act upon OX40 ligand (OX40L), which in turn induces, increases, promotes, stimulates or enhances an activity or function of OX40 by binding to OX40.

Various non-limiting examples of OX40 activities and functions that can be induced, increased, promoted, stimulated or enhanced include, for example, cell proliferation or expansion (e.g., lymphocytes such as activated, effector, memory or regulatory T cells), cell survival or decreasing, inhibiting or preventing apoptosis (e.g., lymphocytes such as activated, effector, memory T cells), cytokine (e.g., Th1, Th2 and non Th1/Th2 cytokines, e.g., IL-17, IL-23 and IL-26) and interferon expression or production such as Th1, Th2, non Th1/Th2, IL-1, IL-2, IL-4, IL-5, IL-6, IL-9, IL-10, IL-14, IL-16, IL-17, IL-23, IL-26, TNF-α, interferon γ, and GM-CSF (in vivo or vitro), anti-apoptotic protein expression or production or suppression or inhibition of pro-apoptotic protein expression or production (e.g., Bcl-xL, Bcl-2, Bad or Bim), inhibition of regulatory t cell development, function or activity, and treatment, prevention or amelioration of disorders, diseases, physiological conditions, pathologies and symptoms thereof. Specific cytokines include but are not limited to IL-1, IL-2, IL-4, IL-5, IL-6, IL-9, IL-10, IL-14, IL-16, IL-17, IL-23, IL-26, TNF-α, interferon γ, and GM-CSF. Specific anti-apoptotic or pro-apoptotic protein expression include but are not limited to Bcl-xL, Bcl-2, Bad and Bim. Other non-limiting activities or functions of OX40 include, for example, activation of NF-kB, maintenance of PKB (Akt) activity, and upregulation of survivin (Ambrosini et al., *Nat. Med.* 3:917 (1997); and Song et al., *Immunity* 22:621 (2005)).

OX40 agonists are therefore characterized as inducing, increasing, promoting, stimulating or enhancing one or more of the recited functions or activities. Thus, an OX40 agonist can be identified as a molecule capable of or by assaying for one or more OX40-mediated signaling or an OX40-mediated or induced function or activity, such as cell proliferation (e.g., activated, effector, memory or regulatory T cells), cell survival or apoptosis (e.g., activated, effector, memory or regulatory T cells), cytokine (e.g., Th1, Th2 and other non Th1/Th2 cytokines, e.g., IL-17, IL-23 and IL-26) and interferon expression or production such as Th1, Th2, non Th1/Th2, IL-1, IL-2, IL-4, IL-5, IL-6, IL-9, IL-10, IL-14, IL-16, IL-17, IL-23, IL-26, TNF-α, interferon γ, and GM-CSF (in vivo or vitro), anti-apoptotic or pro-apoptotic protein expression (e.g., Bcl-xL, Bcl-2, Bad or Bim), and treatment, prevention or amelioration of disorders, diseases, pathologies and symptoms thereof. OX40 agonists also include molecules that induce, increase, promote, stimulate or enhance T cell expansion or survival and numbers of activated, effector or memory T cells, or suppression of regulatory T cells. As set forth herein, OX40 agonists include molecules that exhibit anti-viral activity alone or in combination with antigen, for example, to treat a subject for a viral infection or in connection with immunization or vaccination of a subject against a viral infection.

Exemplary OX40 agonists as set forth herein include polypeptides that bind to OX40, such as OX40L (soluble OX40L), and functional subsequences of OX40L (soluble OX40L) that bind to OX40. Exemplary OX40 agonists as set forth herein also include antibodies and antibody subsequences that bind to OX40. Non-limiting examples of OX40 agonists also include antibodies that bind to OX40 extracellular domain, for example. Exemplary OX40 agonists as set forth herein additionally include antibodies and antibody subsequences that bind to OX40L.

As used herein, the terms "OX40 antibody," "anti-OX40" and "anti-OX40 antibody" refer to an antibody that specifically binds to OX40. Specific binding is that which is selective for an epitope present in OX40. The term "OX40L antibody," "anti-OX40L" and "anti-OX40L antibody" refers to an antibody that specifically binds to OX40L. Specific binding can be distinguished from non-specific binding using assays known in the art (e.g., immunoprecipitation, ELISA, flow cytometry, Western blotting).

Antibodies include monoclonal or polyclonal immunoglobulin molecules that belong to any class such as IgM, IgG, IgA, IgE, IgD, and any subclass thereof. Exemplary subclasses for IgG are $IgG_1$, $IgG_2$, and $IgG_3$. A "monoclonal" antibody refers to an antibody that is based upon, obtained from or derived from a single clone, including any eukaryotic, prokaryotic, or phage clone. A "monoclonal" antibody is therefore defined structurally, and not the method by which it is produced.

Antibodies include full length antibodies that include two heavy and two light chain sequences. Antibodies can have kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa or two lambda light chains.

OX40 antibodies include antibodies, subsequences and fragments capable of binding to OX40 in solution or in solid phase, present on one or more cells in vitro, in primary cell isolates, passaged cells, cultured cells and immortalized cells, or in vivo. Specific non-limiting cell types that can express OX40 include activated and other T cells (e.g., activated, effector, memory or regulatory T cells) and non-T cells. Examples of non-T cells include natural killer (NK) cells, granulocytes (neutrophils), monocytes and B cells. Cells that do not naturally express OX40 can be engineered to express OX40, for example, by transfecting or transforming cells with an OX40 encoding nucleic acid.

Antibodies include mammalian, primatized, humanized, fully human antibodies and chimeras. A mammalian antibody is an antibody which is produced by a mammal, transgenic or non-transgenic, or a non-mammalian organism engineered to produce a mammalian antibody, such as a non-mammalian cell (bacteria, yeast, insect cell), animal or plant.

The term "human" when used in reference to an antibody, means that the amino acid sequence of the antibody is fully human, i.e., human heavy and human light chain variable and human constant regions. Thus, all of the amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest, 4th* Ed. US Department of Health and Human Services. Public Health Service (1987); Chothia and Lesk (1987). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991). Human antibodies therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

Antibodies referred to as "primatized" are "humanized" except that the acceptor human immunoglobulin molecule and framework region amino acid residues may be any primate amino acid residue (e.g., ape, gibbon, gorilla, chimpanzees orangutan, macaque), in addition to any human residue. Human FR residues of the immunoglobulin can be replaced with corresponding non-human residues. Residues in the CDR or human framework regions can therefore be substituted with a corresponding residue from the non-human CDR or framework region donor antibody to alter, generally to improve, antigen affinity or specificity, for example. A humanized antibody may include residues, which are found neither in the human antibody nor in the donor CDR or framework sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., Nature 332:323 (1988)).

The term "chimeric" and grammatical variations thereof, when used in reference to an antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

Methods of producing polyclonal and monoclonal antibodies are known in the art. For example, OX40, or an immunogenic fragment thereof, optionally conjugated to a carrier such as keyhole limpet hemocyanin (KLH) or ovalbumin (e.g., BSA), or mixed with an adjuvant such as Freund's complete or incomplete adjuvant, and used to immunize an animal. Using hybridoma technology, splenocytes from immunized animals that respond to OX40 can be isolated and fused with myeloma cells. Monoclonal antibodies produced by hybridomas can be screened for reactivity with OX40, or an immunogenic fragment thereof. Hybridoma, recombinant, and phage display methods are known in the art (see, for example, U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988).

Animals that may be immunized include primates, mice, rats, rabbits, goats, sheep, cattle, or guinea pigs. Initial and any optional subsequent immunization may be through intravenous, intraperitoneal, intramuscular, or subcutaneous routes. Additionally, to increase the immune response, antigen can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of antigen, and may be at regular or irregular intervals.

Animals include those genetically modified to include human gene loci, which can be used to produce human antibodies. Transgenic animals with one or more human immunoglobulin genes are described, for example, in U.S. Pat. No. 5,939,598, WO 02/43478, and WO 02/092812. Human trans-chromosomic mice (KM Mice™) are described, for example, in WO 02/43478, WO 02/092812, and Ishida, et al., IBC's 11$^{th}$ Antibody Engineering Meeting. Abstract (2000)). In brief, animals are immunized antigen (e.g., OX40, such as OX40-hIgG1 or fusion protein hOX40:hFc or OX40L) or cells that express antigen (e.g., activated human T cells express OX40). Using conventional hybridoma technology, splenocytes from immunized mice that are high responders to the antigen can be isolated and fused with myeloma cells. For example, OX40 antibodies can bind to activated T cells but not resting T cells, or human OX40 transfected cell lines, EL4-OX40 and CHO-OX40, and not non-transformed parental EL4 or CHO cell lines, which indicates that the antibodies specifically bind to OX40. Antibodies that bind to human OX40 may also bind to rhesus macaque OX40 and cynomolgus macaque OX40, but typically do not bind to murine OX40. Human monoclonal antibodies that bind to OX40 can thereby be obtained.

Humanized antibodies can be produced using techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to produce humanized antibodies (Carter et al., *Proc. Natl. Acad. Sci. USA* 89:4285 (1992); and Presta et al., *J. Immunol.* 151:2623 (1993)). Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

OX40 protein suitable for generating antibodies can be produced by any of a variety of standard protein purification or recombinant expression techniques. Forms of OX40 suitable for generating an immune response include OX40 subsequences, such as an immunogenic fragment. Additional forms of OX40 include OX40 expressing cells, OX40 containing preparations or cell extracts or fractions, partially purified OX40. For example, an OX40 sequence can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Suitable techniques that additionally may be employed in antibody methods include OX40-based affinity purification, non-denaturing gel purification, HPLC or RP-HPLC, size exclusion, purification on protein A column, or any combination of these techniques. Antibody isotype can be determined using an ELISA assay, for example, a human Ig can be identified using mouse Ig-absorbed anti-human Ig.

Non-limiting representative examples of antibodies that specifically bind to OX40 include mAb 315, mAb131, mAb 2G2, IF7, ACT35 and mAb L106, and mAb OX86. Antibodies that specifically bind to OX40, denoted as 112F32, 112V8, 112Y55, 112Y131, and 112Z5, which are human monoclonal anti-human OX40 antibodies (human antibodies that bind to human OX40), are described in WO 2007/062445.

OX40 agonists, such as OX40 antibodies include modified forms, such as substitutions (e.g., amino acid substitutions), additions and deletions (e.g., subsequences or fragments), which can be referred to as "variants." Such modified forms and variants can have less than, the same, or greater, but at least a part of, a function or activity of a reference agonist, for example, binding to OX40, or induce, increase, promote, stimulate or enhance an activity or function of OX40 (e.g., OX40 signaling or expression). Thus, a modified agonist can retain at least partial OX40 binding or the ability to induce, increase, promote, stimulate or enhance an activity or function of OX40 (e.g., signaling, expression, a cell response, etc.), for example.

As used herein, the terms "modify" or "variant" and grammatical variations thereof, mean that the composition deviates from a reference composition. Modified and variant agonists may have greater or less activity than or a distinct function from a reference agonist, but at least retain partial OX40 agonist activity. In particular, for example, ability to induce, increase, promote, stimulate or enhance cell proliferation or expansion (e.g., lymphocytes such as activated, effector, memory or regulatory T cells), cell survival or apoptosis (e.g., lymphocytes such as activated, effector, memory or regulatory T cells), cytokine (e.g., Th1, Th2 and non Th1/Th2 cytokines, e.g., IL-17, IL-23 and IL-26) and interferon expression or production (in vivo or vitro), anti-apoptotic or pro-apoptotic protein expression or production and treatment, prevention or amelioration of disorders, diseases, physiological conditions, pathologies and symptoms thereof.

Specific non-limiting examples of agonist modifications and variants include polypeptide subsequences and fragments. The terms "functional subsequence" and "functional fragment" when referring to an agonist means an agonist portion that retains at least a part of one or more functions or activities as full length or native agonist, e.g., a function or activity of OX40 agonist. For example, an antibody subsequence or fragment that binds to OX40, or a fragment of OX40L is considered a functional subsequence. Thus, OX40 antibody subsequences or fragments retain, at least a part of, a function or activity of an unmodified or a reference OX40 full length, native or intact antibody. Subsequences and fragments can have less than, the same, or greater OX40 binding affinity as full length molecule, the binding specificity as full length molecule, or one or more activities or functions of as a full length molecule, e.g., a function or activity of OX40 agonist.

Exemplary subsequences and fragments include antibody subsequences and fragments that bind to OX40 and a portion of an OX40L sequence that binds to OX40. A subsequence of an OX40 or OX40L molecule or antibody has at least one fewer amino acid than a full length OX40 or OX40L molecule or antibody (e.g., one or more internal or terminal amino acid deletions from either amino or carboxy-termini of OX40, OX40L or a full length antibody having two heavy chains and two light chains that binds to OX40). Non-limiting representative subsequences of a full length antibody are Fab, Fab', F(ab')$_2$, Fv, Fd, single-chain Fv (scFv), disulfide linked Fv (sdFv), light chain variable (VL) and heavy chain variable (VH).

Antibody subsequences and fragments can be combined. For example, $V_L$ or $V_H$ subsequences can be joined by a linker sequence thereby forming a $V_L$-$V_H$ chimera. A combination of single-chain Fvs (scFv) subsequences can be joined by a linker sequence thereby forming an scFv-scFv chimera. Antibody subsequences and fragments include single-chain antibodies or variable region(s) alone or in combination with all or a portion of other antibody subsequences.

Variant polypeptides include those with one or more amino acid substitutions and additions. Antibodies with substitutions can be within or outside of a constant region, a complementary determining region (CDR) or a framework (FR) region. A particular non-limiting example is an amino acid substitution, such as a conservative substitution within or outside of a constant region, a complementary determining region (CDR) or a framework (FR) region.

A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Modified polypeptides also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond.

Polypeptide sequences including modified forms can be made using recombinant DNA technology via cell expression or in vitro translation. Polypeptide sequences including modified forms can also be produced by chemical synthesis using methods known in the art, for example, an automated peptide synthesis apparatus (see, e.g., Applied Biosystems, Foster City, Calif.).

Antibody subsequences and fragments can be prepared by proteolytic hydrolysis of antibody, for example, by pepsin or papain digestion of whole antibodies. Antibody subsequences and fragments produced by enzymatic cleavage with pepsin provide a 5S fragment denoted F(ab')$_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used.

Viruses and viral infections that may be vaccinated or immunized or treated in accordance with the invention include a poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus and retrovirus.

Non-limiting examples of poxvirus include a vaccinia virus, *Molluscum contagiosum*, variola major or variola minor smallpox virus, cow pox, camel pox, sheep pox, and monkey pox.

Non-limiting examples of herpesvirus include an alpha-herpesvirus, beta-herpesvirus, gamma-herpesvirus, Epstein Bar Virus (EBV), Cytomegalovirus (CMV), varicella zoster virus (VZV/HHV-3), and human herpes virus 1, 2, 4, 5, 6, 7, and 8 (HHV-8, Kaposi's sarcoma-associated virus).

Non-limiting examples of hepatitis virus include hepatitis A, B, C, D, E and G.

Non-limiting examples of immunodeficiency virus include human immunodeficiency virus (HIV), such as HIV-1, HIV-2 and HIV-3.

Non-limiting examples of flavivirus include Yellow Fever virus, Dengue virus, Japanese Encephalitis and West Nile viruses.

Non-limiting examples of papilloma virus include a human papilloma virus (HPV), such as HPV strain 1, 6, 11, 16, 18, 30, 31, 42, 43, 44, 45, 51, 52, and 54.

Non-limiting examples of polyoma virus include BK virus (BKV) and JC virus (JCV).

Non-limiting examples of rhabdovirus include rabies virus and vesiculovirus.

Non-limiting examples of myxovirus include paramyxovirus and orthomyoxovirus. Non-limiting examples of paramyxovirus include measles, mumps, pneumovirus and respiratory syncytial virus (RSV).

Non-limiting examples of orthomyoxovirus include influenza virus, such as influenza A, influenza B and influenza C.

Non-limiting examples of arenavirus include lymphocytic choriomeningitis virus (LCMV), Junin virus, Lassa virus, Guanarito virus, Sabia virus and Machupo virus.

Non-limiting examples of coronavirus include a virus that causes a common cold, and severe acute respiratory syndrome (SARS).

Non-limiting examples of adenovirus include viral infections of bronchii, lung, stomach, intestine (gastroenteritis), eye (conjunctivitis), bladder (cystitis) and skin.

Non-limiting examples of reovirus include a rotavirus, cypovirus and orbivirus.

Non-limiting examples of picornavirus include a rhinovirus, apthovirus, hepatovirus, enterovirus and cardiovirus. Rhinovirus can cause the common cold.

Non-limiting examples of togavirus include alphavirus, sindbus virus, and rubellavirus.

Non-limiting examples of bunyavirus include hantavirus, phlebovirus and nairovirus.

Non-limiting examples of retrovirus include an alpha, beta, delta, gamma, epsilon, lentivirus, spumavirus and human T-cell leukemia virus.

Non-limiting examples of lentivirus include an immunodeficiency virus, such as immunodeficiency virus (e.g., a bovine, porcine, equine, canine, feline or primate virus).

Non-limiting examples of human T-cell leukemia viruses include human T-cell leukemia virus 1 and 2 (HTLV-1 and HTLV-2).

Viral antigen, or live or attenuated virus, useful in accordance with the invention methods and compositions include any viral antigen, or live or attenuated virus, that can or is likely to provide protection against a virus, or can or is likely to be a component of a vaccine or used as an immunizing antigen. Non-limiting examples include a viral antigen, or live or attenuated virus, of a poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or a retrovirus.

Poxvirus viral antigens, or live or attenuated virus, include a vaccinia virus, *Molluscum contagiosum*, variola major or variola minor smallpox virus, cow pox, camel pox, sheep pox, or monkey pox antigen, or live or attenuated virus. Non-limiting specific examples include B8R, L4R, H3L, E9L, F15L, J4R, I1L, A3L, A8R, A23R or B2R antigen.

Herpesvirus antigens, or live or attenuated virus, include an alpha-herpesvirus, beta-herpesvirus, gamma-herpesvirus, Epstein Bar Virus (EBV), Cytomegalovirus (CMV), varicella zoster virus (VZV/HHV-3), or human herpes virus 1, 2, 4, 5, 6, 7, or 8 (HHV-8, Kaposi's sarcoma-associated virus) antigen, or live or attenuated virus. Non-limiting proteins include envelope protein (e.g., glycoprotein gp42, gp350, gpK8.1A, B, C, D, E, H, L (gB, gC, gD, gE, gH, gL)), tegument protein (e.g., UL17, UL36, UL37, UL48, UL49, US11, UL11, UL14, UL16, UL21, UL41, UL46, UL47, VP13/14, VP16, VP22, etc.), capsid protein (e.g., VP5, VP19c, VP21, VP23, VP24, VP26, etc.), core protein and polymerase.

Hepatitis viral antigen, or live or attenuated virus, include a hepatitis A, B, C, D, E or G viral antigen, or live or attenuated virus.

Immunodeficiency virus antigens, or live or attenuated virus, include HTLV and human immunodeficiency virus (HIV) antigen, or live or attenuated virus. Exemplary HIV antigen includes HIV-1, HIV-2 or HIV-3 antigen, or attenuated virus. Non-limiting proteins include envelope protein gp160, gp120 or gp41, gag protein, pol protein, p17, p17, p24, tat, rev, nef, vif, vpr, vpu, reverse transcriptase, integrase, or protease).

Flavivirus antigens, or live or attenuated virus, include Yellow Fever virus, Dengue virus, Japanese Encephalitis and West Nile virus antigen, or live or attenuated virus.

Papilloma virus antigen, or live or attenuated virus, includes a human papilloma virus (HPV) antigen, or live or attenuated virus. Non-limiting specific human papilloma virus antigen examples include an HPV strain 1, 6, 11, 16, 18, 30, 31, 42, 43, 44, 45, 51, 52, or 54 antigen.

Polyoma virus antigen, or live or attenuated virus, include a BK virus (BKV) or JC virus (JCV) antigen, or live or attenuated virus.

Rhabdovirus antigen, or live or attenuated virus, includes a rabies virus or vesiculovirus antigen, or live or attenuated virus.

Myxovirus antigen, or live or attenuated virus, includes a paramyxovirus or orthomyoxovirus antigen, or live or attenuated virus. Exemplary paramyxovirus antigen, or live or attenuated virus, includes a measles, mumps, pneumovirus or respiratory syncytial virus (RSV) antigen, or live or attenuated virus.

Orthomyoxovirus antigen, or live or attenuated virus, includes an influenza virus antigen, or live or attenuated virus. Non-limiting specific examples of influenza virus antigen, or live or attenuated virus, include influenza A, influenza B and influenza C viral antigen, or live or attenuated virus. Non-limiting influenza virus proteins include one or more present on A/PR/34, A/HK8/68, A/HK/1/68, H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N$_3$.

Arenavirus antigen, or live or attenuated virus, includes a lymphocytic choriomeningitis virus (LCMV), Junin virus, Lassa virus, Guanarito virus, Sabia virus or Machupo virus antigen, or live or attenuated virus.

Coronavirus antigen, or live or attenuated virus, includes an antigen of a virus that causes a common cold or severe acute respiratory syndrome (SARS).

Reovirus antigen, or live or attenuated virus, include a rotavirus, cypovirus or orbivirus antigen, or live or attenuated virus.

Picornavirus antigen includes a rhinovirus, apthovirus, hepatovirus, enterovirus or cardiovirus antigen.

Togavirus antigen, or live or attenuated virus, includes an alphavirus, sindbus virus, or rubellavirus antigen, or live or attenuated virus.

Bunyavirus antigen, or live or attenuated virus, includes a hantavirus, phlebovirus or nairovirus antigen, or live or attenuated virus.

Retrovirus antigen, or live or attenuated virus, includes an alpha, beta, delta, gamma, epsilon, lentivirus, spumavirus or human T-cell leukemia virus antigen. Lentivirus antigen includes an immunodeficiency virus antigen, or live or attenuated virus. Immunodeficiency virus antigen, or live or attenuated virus, includes a bovine, porcine, equine, canine, feline or primate virus antigen, or live or attenuated virus. Human T-cell leukemia virus antigen, or live or attenuated virus, includes a human T-cell leukemia virus 1 or 2 (HTLV-1 and HTLV-2) antigen, or live or attenuated virus.

Invention methods and compositions, among other things, include vaccination or immunizing a subject against a viral infection, as well as treating a subject for a viral infection. Such methods can result in providing the subject with at least some protection from a viral infection (e.g., prophylactic protection) or result in treatment of an existing viral infection (e.g., therapeutic treatment).

In particular methods embodiments, one or more disorders, diseases, physiological conditions, pathologies and symptoms associated with or caused by a viral infection will respond to treatment or therapy with an OX40 agonist. In particular methods embodiments, treatment methods include protecting against a virus infection or pathology, reduce, decrease or inhibit susceptibility to virus infection or pathology, reduce, decrease or inhibit virus titer, reduce, decrease or inhibit virus proliferation, reduce, decrease or inhibit the amount of a virus protein, or reduce, decrease or inhibit the amount of a virus nucleic acid. In particular methods embodiments, treatment methods include an amount of OX40 agonist sufficient to increase or stimulate CD4 or CD8 T cell priming, to increase or stimulate virus clearance, reduce, decrease or inhibit virus infection, reduce, decrease or inhibit increases in virus titer, reduce, decrease or inhibit virus proliferation or replication, reduce, decrease or inhibit synthesis of a virus protein or a virus nucleic acid, or reduce, decrease or inhibit virus reactivation from latency.

Methods of the invention include methods in which treatment results in any beneficial or therapeutic effect. In various methods embodiments, virus infection or pathogenesis is reduced, decreased, inhibited, delayed or prevented, or a method alleviates or ameliorates one or more adverse (physical) symptoms or complications, e.g., prevents, decreases, reduces or improves one or more physiological conditions, disorders, illnesses, diseases or symptoms caused by or associated with chronic or acute virus infection, pathology or reactivation. In various further particular embodiments, treatment methods include reducing, decreasing, inhibiting or preventing onset, progression, frequency, duration, severity, probability or susceptibility of one or more adverse symptoms or complications associated with or caused by chronic or acute virus infection, pathology or reactivation. In still further embodiments, treatment methods include accelerating or facilitating or hastening recovery of a subject from a viral infection or pathogenesis or one or more adverse symptoms or complications thereof, or decreasing, preventing, reducing, inhibiting, or delaying an adverse side effect or complication associated with or caused by vaccination or immunization. In yet additional embodiments, treatment methods include stabilizing infection, pathogenesis, or an adverse symptom or complication associated with or caused by virus infection or pathogenesis.

A beneficial or therapeutic effect is therefore any objective or subjective measurable or detectable improvement or benefit provided to a particular subject. A beneficial or therapeutic effect can but need not be complete ablation of any particular symptom or all symptoms, adverse side effects or complications associated with or caused by virus infection or pathogenesis. Thus, a satisfactory clinical endpoint is achieved when there is an incremental improvement or a partial reduction in an adverse symptom or complication, or an inhibition or prevention of worsening or progression of the symptom or condition, over a short or long duration (hours, days, weeks, months, etc.).

A beneficial or therapeutic effect also includes reducing or eliminating the need, dosage frequency or amount of an antiviral drug or other agent (e.g., protein, antibody) used for treating a subject having or at risk of having a virus infection or pathogenesis, or vaccinating or immunizing a subject. For example, reducing an amount of viral antigen (e.g., live or attenuated virus, extracts, or protein) used for immunization or vaccination of a subject against a virus infection is also considered an improvement.

Adverse symptoms and complications associated with poxvirus (vaccinia virus) infection and pathogenesis include, for example, high fever, fatigue, headache, backache, malaise, rash (maculopapular, vesicular or pustular) or lesions, delirium, vomiting, diarrhea, and excess bleeding. Other symptoms of poxvirus infection or pathogenesis, including variola major and variola minor smallpox virus, monkeypox, cowpox, *Molluscum contagiosum* and camelpox, are known in the art and treatment thereof in accordance with the invention is provided.

Adverse symptoms and complications associated with herpesvirus infection and pathogenesis include, for example, red skin, blisters, pustules, bumps, healing with skin regeneration, pain, burning or itching in affected area, swollen lymph glands, headache, muscle ache, fever, burning sensation during urination, lower back pain, pox (e.g., chickenpox). Other symptoms of herpesvirus infection or pathogenesis are known in the art and treatment thereof in accordance with the invention is provided.

Adverse symptoms and complications associated with hepatitis infection and pathogenesis include, for example, abdominal pain, jaundice, flu-like illness, nausea, vomiting, diarrhea, loss of appetite, weight loss, joint pain, fatigue, and itchy skin. Other symptoms of hepatitis infection or pathogenesis are known in the art and treatment thereof in accordance with the invention is provided.

Adverse symptoms and complications associated with immunodeficiency virus (e.g., HIV) infection and pathogenesis include, for example, abdominal cramps, nausea, vomiting, diarrhea, enlarged lymph nodes, fever, headache, muscle ache or pain, skin rash, sore throat, weight loss, loss of T cells (CD4+), increased frequency of opportunistic infections, such as yeast and bacterial infections. Other symptoms of immunodeficiency virus infection or pathogenesis are known in the art and treatment thereof in accordance with the invention is provided.

Adverse symptoms and complications associated with flavirus (e.g., west nile virus) infection and pathogenesis include, for example, acute febrile illness, malaise, headache, flushing, and diarrhea. Other symptoms of flavirus infection or pathogenesis are known in the art and treatment thereof in accordance with the invention is provided.

Adverse symptoms and complications associated with papillomavirus (PPV) infection and pathogenesis include, for example, warts (e.g., genital warts). Other symptoms of papillomavirus infection or pathogenesis are known in the art and treatment thereof in accordance with the invention is provided.

Additional disorders, diseases, physiological conditions, pathologies and adverse symptoms and complications associated with or caused by a viral infection will of course depend upon the particular virus type, stage of infection, the particular subject infected, etc. Specific disorders would be known by the skilled artisan.

Methods and compositions of the invention include administration of an amount of OX40 agonist to a subject thereby increasing numbers or activation of an immune cell (e.g., dendritic cells, T cells, CD4+ cells, CD8+ cells, etc.) with or at risk of a viral infection. A subject can be administered OX40 agonist alone or in combination with viral antigen, or live or attenuated virus, prior to contact, substantially contemporaneously with or following vaccination or immunization of the subject against the virus infection by a virus, as well as treatment substantially contemporaneously with or after a subject has been contacted by, exposed to or infected with a virus.

Methods and compositions of the invention include increasing or inducing an antiviral CD8+ T cell response in a subject with or at risk of a viral administration. In one embodiment, a method includes administering to a subject an amount of OX40 agonist sufficient to increase or induce or increase antiviral CD8+ T cell response in the subject.

Methods and compositions of the invention include administration of an OX40 agonist to a subject prior to contact, exposure or infection by a virus, as well as treatment substantially contemporaneously with or after a subject has been contacted by, exposed to or infected with a virus. Methods and compositions of the invention also include administration of an OX40 agonist to a subject prior to vaccinating or immunizing a subject against a virus, vaccinating or immunizing substantially contemporaneously with or after a subject has been contacted by, exposed to or infected with a virus, as well as vaccinating or immunizing after a subject has been contacted by, exposed to or infected with a virus. A subject infected with a virus may have an acute infection or be chronically infected over a period of days, months, or years.

Methods and compositions of the invention include administration of OX40 agonist to a subject prior to contact, substantially contemporaneously with or following administration of a viral antigen to the subject. A subject can be administered OX40 agonist alone or in combination with viral antigen prior to contact, substantially contemporaneously with or following vaccination or immunization of the subject against the virus. OX40 agonist can therefore be administered to a subject in a combination with a viral antigen, or live or attenuated virus, or separately, i.e., the OX40 and viral antigen, or live or attenuated virus, are administered sequentially to a subject.

Invention compositions and methods can be combined with any compound, agent, treatment or other therapeutic regimen having a desired therapeutic, beneficial, additive, synergistic or complementary activity or effect. Exemplary treatments and therapies include anti-viral agents or drugs, as well as agents that assist, promote, stimulate or enhance vaccination or immunization efficacy. Such anti-viral drugs, agents, treatments and therapies can be performed prior to, substantially contemporaneously with or following any other methods of the invention, for example, a method of treating a subject for a viral infection or a method of vaccinating or immunizing a subject against a viral infection.

Combination methods embodiments include, for example, anti-viral drugs, such as protease inhibitors, reverse transcriptase inhibitors, virus fusion inhibitors and virus entry inhibitors, antibodies to viral proteins, live or attenuated virus, immune stimulating agents, etc., and include contact with, administration in vitro or in vivo, with another compound, agent, treatment or therapeutic regimen appropriate for viral infection, vaccination or immunization Specific non-limiting examples of antivirals include AK602, AMD070, APV, ATV, ATZ, AVX754, AZT, Abacavir, Acyclovir, Adefovir dipivoxil, Adriamycin, Agenerase, Aldesleukin, Alovudine, AmBisome, Amdoxovir, Amphocin, Amphotec, Amphotericin B, Ampligen, Amprenavir, Androderm, Androgel, Aptivus, Atazanavir, Azithromycin, BMS-488043, Bactrim, Baraclude, Biaxin, Buffer-Gel, C31G, CD4-IgG2, CPV, CS, Calanolide A, Capravirine, Carbopol 974P, Carrageenan, Carraguard, Cellulose sulfate, Cidofivir, Clarithromycin, Combivir, Copegus, Cotrimoxazole, Crixivan, Cyanovirin-N, Cytovene, DAPD, DLV, DPC 817, DS, Delavirdine, Depo-Testosterone, Dextran sulfate, Didanosine, Diflucan, Doxil, Doxorubicin, Dronabinol, Duofilm, EFV, Efavirenz, Elvucitabine, Emtricitabine, Emtriva, Enfuvirtide, Entecavir, Epivir, Epoetin alfa, Epogen, Epzicom, Etopophos (phosphate salt), Etoposide, Etravirine, Fluconazole, Fortovase, Fosamprenavir, Fungizone, Fuzeon, GSK-873,140 (aplaviroc), GW433908, Gammar-P, Ganciclovir, Growth hormone, Human growth hormone, HEC, Hepsera, Hivid, Hydroxyethyl cellulose, IDV, IGIV, Imiquimod cream, Interleukin-2 (IL-2), INH, Immune Globulin, Indinavir, Interferon alfa-2, Interferon alfa-2b, Intron A (2b), Invirase, Isoniazid, Itraconazole, KP-1461, Kaletra, L-000870810, LPV/RTV, Lamivudine, Lexiva, Marinol, Megace, Megestrol, Mycobutin, NFV, NVP, Naphthalene 2-sulfonate polymer, Nebupent, Nelfinavir, Neutrexin, Nevirapine, New-Fill, Norvir, Nydrazid, Occlusal, Onxol, Oseltamivir, PA-457, PMPA, PRO 2000, PRO 542, Paclitaxel, Paxene, Pegasys (2a), Pentamidine, Peptide T, pleconaril, podofilox, podophyllin, Poly(I)-Poly(C12U), Poly-L-lactic acid, Polygam S/D, Procrit, Proleukin, RCV, RTV, RVT, Racivir, Rebetol, Rescriptor, Retrovir, Reverset, Reyataz, Ribavirin, Rifabutin, Rifadin, Rifampin, Rimactane, Ritonavir, Roferon-A (2a), SCH-C, SCH-D (vicriviroc), SQV, Saquinavir, Savvy, Sculptra, Septra, Serostim, Somatropin, Sporanox, Stavudine, Sulfamethoxazole, Sustanon, Sustiva, T-20, TDF, THC, TMC114, TMC125, TNX-355, Taxol, Tenofovir, Tenofovir disoproxil fumarate, Testosterone, Tipranavir, Toposar, TransVer-S al, Trichloroacetic acid (TCA), Trimethoprim, Trimetrexate, Trizivir, Truvada, UC-781, UK-427,857 (maraviroc), Ushercell, Valcyte, Valganciclovir, Valproic acid, VePesid, Vicriviroc, Videx, Viracept, Viranol, Viramune, Virazole, Viread, Vitrasert, ZDV, Zalcitabine, Zerit, Ziagen, Zidovudine, Zithromax, Zovirax, D4T, ddC, β-LFddC, P-LFd4C, DDI, f-APV, 3TC, 5-FU and human erythropoietin (EPO).

Specific non-limiting examples of combination embodiments include treatments such as steroidal and non-steroidal anti-inflammatory drugs such as acetaminophen, ibuprofen, naproxen, indomethacin, piroxicam, ketoprofen and pyrancarboxylic acid (Lodine).

Viral antigens (e.g., protein), or live or attenuated virus, inactivated virus, virus extract, antibody that binds to viral protein, viral nucleic acid, and passive vaccination are useful in accordance with the methods of the invention. Further additional exemplary treatments include viral protein, antibody that binds to viral protein, viral nucleic acid, passive vaccination such as VIG and vaccination with inactivated virus, virus extract, live virus or attenuated virus.

The invention provides combinations in which a method of the invention is used in a combination with any agent, drug, therapeutic regimen, treatment protocol, process, remedy or composition, such as an anti-viral or vaccination/immunization protocol, agent or drug set forth herein or known in the art. In one embodiment, a method includes administering an OX40 agonist and an anti-viral or vaccination/immunization agent, drug, treatment, protocol, process, remedy or composition. The anti-viral or vaccination/immunization agent, drug, treatment, protocol or composition can be administered with the OX40 agonist, or prior to, substantially contemporaneously with or following administration of OX40 agonist to a subject.

Methods of the invention also include, among other things, methods that result in a reduced need or use of another agent, drug, therapeutic regimen, treatment protocol, process, remedy or composition. For example, for a viral infection, vaccination or immunization, a method of the invention has a therapeutic benefit if in a given subject a less frequent or reduced dose or elimination of an anti-viral treatment or therapy results. Thus, in accordance with the invention, methods of reducing need or use of an anti-viral treatment or therapy are provided.

In invention methods in which there is a desired outcome, such as a prophylactic or therapeutic method that provides an objective or subjective benefit from vaccination or immunization or treatment of a viral infection or pathogenesis, an OX40 agonist alone or in combination with another composition, such as a viral antigen, can be administered in a sufficient or effective amount. As used herein, a "sufficient amount" or "effective amount" or an "amount sufficient" or an "amount effective" refers to an amount that provides, in single or multiple doses, alone or in combination with one or more other treatments, therapeutic regimens or agents (e.g., a drug), a long term or a short term detectable or measurable improvement in a given subject or a benefit to a given subject of any degree or for any time period or duration (e.g., for minutes, hours, days, months, years, or cured).

An amount sufficient or an amount effective can but need not be provided in a single administration and can but need not be achieved by an OX40 agonist alone or in combination with a viral antigen, live or attenuated virus, another compound, agent, treatment or therapeutic regimen. In addition, an amount sufficient or an amount effective need not be sufficient or effective if given in single or multiple doses without a second or additional viral antigen, live or attenuated virus, compound, agent, treatment or therapeutic regimen, since additional doses, amounts or duration above and beyond such doses, or additional antigens, live or attenuated virus, drugs, agents, treatment or therapeutic regimens may be included in order to provide a given subject with a detectable or measurable improvement or benefit to the subject.

An amount sufficient or an amount effective need not be prophylactically or therapeutically effective in each and every subject treated, nor a majority of subjects treated in a given group or population. An amount sufficient or an amount effective means sufficiency or effectiveness in a particular subject, not a group or the general population. As is typical for such methods, subjects will exhibit varied responses to treatment, vaccination and immunization methods.

The term "subject" refers to an animal, typically a mammalian animal, such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, the mouse models of virus infection exemplified herein.

Subjects appropriate for treatment include those having or at risk of having a viral infection or pathogenesis. Target subjects therefore include subjects that have been exposed to or contacted with a virus, or that have developed one or more adverse symptoms caused by or associated with virus infection or pathogenesis, regardless of the type, timing or degree of onset, progression, severity, frequency, duration of the symptoms.

Target subjects also include those at risk of virus exposure, contact, infection or pathogenesis or at risk of having or developing a viral infection or pathogenesis. The invention methods are therefore applicable to treating a subject who is at risk of virus exposure, contact, infection or pathogenesis, but has not yet been exposed to or contacted with virus. Prophylactic methods are therefore included. Target subjects for prophylaxis can be at increased risk (probability or susceptibility) of virus exposure, contact, infection or pathogenesis, as set forth herein and known in the art. Target subjects need not be at increased risk, but may be from the general population in which it is desired to vaccinate or immunize subjects against a viral infection. For example, a subject at risk of exposure to or contact with a poxvirus. Another non-limiting example is a subject such as an infant which typically receives a vaccination or immunization against mumps, measles, rubella or polio are candidate subjects. Another non-limiting example is a subject at risk of papilloma virus infection, which can cause various cancers.

At risk subjects appropriate for treatment also include subjects exposed to other subjects having a virus infection or having been exposed to another subject having a virus infection. Subjects appropriate for treatment therefore include human subjects exposed to or at risk of exposure to other humans that may have a virus infection, or are at risk of a virus infection. At risk subjects appropriate for treatment also include subjects where the risk of virus infection or pathogenesis is increased due to changes in virus infectivity or cell tropism, environmental factors, or immunological susceptibility (e.g., an immune-suppressed, immunocompromised, or HIV-positive subject).

"Prophylaxis" and grammatical variations thereof mean a method in which contact, administration or in vivo delivery to a subject is prior to contact with or exposure to virus, or vaccination or immunization of a subject against a virus. In certain situations it may not be known that a subject has been contacted with or exposed to virus, or vaccinated or immunized against a virus, but administration or in vivo delivery to a subject can be performed prior to virus infection or manifestation of pathogenesis (or an associated symptom). In either case, a method can eliminate, prevent, inhibit, decrease or reduce the probability of or susceptibility towards a virus infection or pathogenesis, or an adverse symptom or complication associated with or caused by virus infection or pathogenesis.

Methods of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intra-spinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic.

OX40 agonists and viral antigen, live or attenuated virus, can be administered in accordance with the methods as a single or multiple dose e.g., one or more times daily, weekly, monthly or annually or between about 1 to 10 weeks, or for as long as appropriate, for example, to achieve a reduction in the onset, progression, severity, frequency, duration of one or more symptoms or complications associated with or caused by virus infection or pathogenesis. Thus, a method can be practiced one or more times (e.g., 1-10, 1-5 or 1-3 times) a day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

Doses can be based upon current existing protocols, empirically determined, determined using animal disease models or optionally in human clinical trials. Initial study doses can be based upon animal studies set forth herein, for a mouse, which weighs about 30 grams, and the amount of OX40 agonists with or without viral antigen administered that is determined to be effective. Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1, 000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg. 0-25 mg/kg, or 1.0-10 mg/kg, or any numerical value or range or value within such ranges.

Doses can vary and depend upon whether the treatment is prophylactic or therapeutic, the onset, progression, severity, frequency, duration probability of or susceptibility of the symptom, the type of virus infection or pathogenesis to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a prophylactic or therapeutic benefit.

Typically, for therapeutic treatment, OX40 agonists with or without viral antigen, live or attenuated virus, will be administered as soon as practical, typically within 1-2, 2-4, 4-12, 12-24 or 24-72 hours after a subject is exposed to or contacted with a virus, or within 1-2, 2-4, 4-12, 12-24 or 24-48 hours after onset or development of one or more symptoms associated with or caused by a virus infection or pathogenesis. For prophylactic treatment, OX40 agonists with or without viral antigen, live or attenuated virus, can be administered for a duration of 0-4 weeks, e.g., 2-3 weeks, prior to exposure to or contact with virus. For prophylactic treatment in connection with vaccination or immunization of a subject OX40 agonists with or without viral antigen, live or attenuated virus, can be administered prior to, concurrently with or following immunization or vaccination. Typically, OX40 agonists are administered concurrently with viral antigen, live or attenuated virus, vaccination or immunization of a subject, but can be administered within 1-2, 2-4, 4-12, 12-24 or 24-48 hours prior to vaccination or immunization or within 1-2, 2-4, 4-12, 12-24 or 24-48 hours following vaccination or immunization. For a chronic infection, doses, OX40 agonists with or without viral antigen, live or attenuated virus, are administered at any time.

The dose amount, number, frequency or duration may be proportionally increased or reduced, as indicated by the status of the subject. For example, whether the subject has a virus infection or pathogenesis, whether the subject has been exposed to or contacted with virus or is merely at risk of virus contact or exposure, or whether the subject is a candidate for or will undergo vaccination or immunization with virus. The dose amount, number, frequency or duration may be proportionally increased or reduced, as indicated by any adverse side effects, complications or other risk factors of the treatment or therapy.

OX40 agonists and viral antigen, live or attenuated virus, can be incorporated into pharmaceutical compositions. Such pharmaceutical compositions are useful for administration to a subject in vivo or ex vivo.

OX40 agonists and viral antigen, live or attenuated virus, can be included in a pharmaceutically acceptable carrier or excipient prior to administration to a subject. As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, ophthalmic, optical, intravenous (i.v.), intramuscular, intraglandular, intraorgan, intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9->2-hydroxy-ethoxy methyl guanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technomic Publishing Co., Inc., Lancaster, Pa.; *Ansel and Stoklosa, Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

OX40 agonists and viral antigen, live or attenuated virus, can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

The invention provides kits comprising OX40 agonists alone and with viral antigen, live or attenuated virus, combination compositions and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., OX40 agonist and viral antigen, live or attenuated virus, alone or in combination.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder or disease (e.g., viral infection, vaccination or immunization) for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or prophylactic or therapeutic regimes described herein. Exemplary instructions include, instructions for treating a virus infection or pathogenesis, and instructions for vaccinating or immunizing a subject. Kits of the invention therefore can additionally include labels or instructions for practicing any of the methods of the invention described herein including treatment, detection, monitoring or diagnostic methods. Thus, for example, a kit can include an antibody that has one or more anti-viral functions or activities as set forth herein, together with instructions for administering the antibody in a prophylactic or therapeutic treatment method of the invention.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to an "OX40 agonist" or a "viral antigen, live or attenuated virus" includes a plurality of such agonists, antigens or virus and reference to an "activity or function" such as "an OX40 activity or function" can include reference to one or more activities or functions, and so forth.

As used herein, all numerical values or ranges include fractions of the values and integers within such ranges and fractions of the integers within such ranges unless the context clearly indicates otherwise. Thus, to illustrate, reference to a numerical range, such as a percentage range, 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. For example, in certain embodiments or aspects of the invention, agonists or antigens or other materials and method steps are excluded. In certain embodiments and aspects of the invention, an OX40 agonist or a viral antigen is excluded. Thus, even though the invention is generally not expressed herein in terms of what the invention does not include, embodiments and aspects that expressly exclude compositions (e.g., agonists or viral antigens) and method steps are nevertheless disclosed and included in the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This examples describes various materials and methods.

Mice were 8-12 wk-old female and male C57BL/6. Mice were purchased from the Jackson Laboratory (Bar Harbor, Me.).

The vaccinia virus Western Reserve ($VV_{WR}$) strain was purchased from the American Type Culture Collection (Manassas, Va.), grown in HeLa cells, and titered on Vero cells (Davis et al. 2005). Vaccinia virus New York City Board of Health ($VV_{NYBOH}$) stocks were generated as low-passage stocks from commercial Dryvax, using the same conditions as $VV_{WR}$ above.

For live virus immunization, the Western Reserve strain of vaccinia virus ($VV_{WR}$) was purified by sucrose gradient centrifugation and diluted with PBS to a titer of $10^9$ PFU per ml, and aliquots stored at −80° C. For most studies, mice were infected intraperitonealy (i.p.) with $2\times10^5$ PFU of VV-WR. For dermal scarification, virus (10 µl) was deposited at the base of the tail, and the skin at the site of the droplet was scarified 25 to 30 times with a 25-gauge needle. After 3 to 4 days, pustules or scabs were observed at the scarification site, indicating a localized vaccinia virus infection. Groups of mice received 150 µg/mouse of an agonistic anti-OX40 mAb (OX86) or an isotype control rat IgG mAb. T cell responses were analyzed in the spleens of infected mice on day 8 postinfection (PI).

For vaccinia virus challenge, one day prior to challenge, serum samples were collected and mice were weighed. On the day of challenge, an aliquot of purified $VV_{WR}$ was thawed, sonicated, and diluted in PBS. Mice were anesthetized by inhalation of isoflurane and inoculated by the intranasal (i.n.) route with a 10-µl suspension of $3.5\times10^8$ of $VV_{WR}$. Mice were weighed daily for 2 weeks following challenge and were euthanized when they lost 25% of their initial body weight. For protection experiments, mice were vaccinated subcutaneously (s.c.) at the base of the tail once with either 10 µg/mouse of class I restricted CD8 T cell peptide epitopes (B8R, A3L, A8R, A23R, and B2R) emulsified in IFA or 30 µg/mouse of class II restricted CD4 T cell peptide epitopes (L4R, H3L, E9L, F15L, and J4R) emulsified in CFA. One day later, groups of mice received 150 µg/mouse of an agonistic anti-OX40 mAb (OX86) or an isotype control rat IgG mAb. Weight loss was monitored for 2 wk with measurement of individual body weights every day and scoring signs. Clinically impaired mice with severe systemic infection and having lost >25% of body weight were euthanized. The mean change in body weight was calculated as percentage of the mean weight for each group on the day of challenge.

For cell surface and intracellular staining of T cells, flow cytometric measurement of cytokine production in T cells was done after lysing red blood cells (RBCs), and splenocytes from infected mice were resuspended in RPMI-1640 medium (Gibco) supplemented with 10% FCS (Omega Scientific), 1% L-glutamine (Invitrogen), 100 µg/ml streptomycin, 100 U/ml penicillin and 50 µM 2-mercaptoethanol (Sigma). $1-2\times10^6$ cells were plated in round-bottomed 96-well microtiter plates in 200 µl with medium or the indicated VV derived peptides (final concentration of 1 µg/ml and 5 µg/ml for class I and class II restricted peptides respectively) for 1 hrs at 37° C. GolgiPlug (BD Biosciences) was then added to the cultures according to the manufacture's instructions and the incubation continued for 7 hrs. At the end of the culture cells were harvested, washed twice in PBS plus 2% BSA buffer, stained with anti-CD8 (PerCP) or anti-CD4 (PerCP) and CD62L (PE), followed by fixation with cytofix-cytosperm (BD Biosciences) for 20 min at 4° C. Fixed cells were washed two times in 1×BD Perm/Wash solution and subjected to intracellular cytokine staining in BD Perm/Wash buffer for 30 min at 4° C. Anti-IFN-γ (APC) was obtained from e-Biosience and used at a 1:100 dilution. Samples were analyzed for their proportion of cytoplasmic cytokines after gating on CD8+CD62L-$_{low}$ T cells by FACSCalibur™ flow cytometer using CellQuest (BD Biosciences) and FlowJo software (Tree Star, San Carlos, Calif.).

Example 2

This example includes a description of data indicating that CD8 and CD4 T cell responses to Vaccinia virus are enhanced following anti-OX40 treatment.

Figure 1:
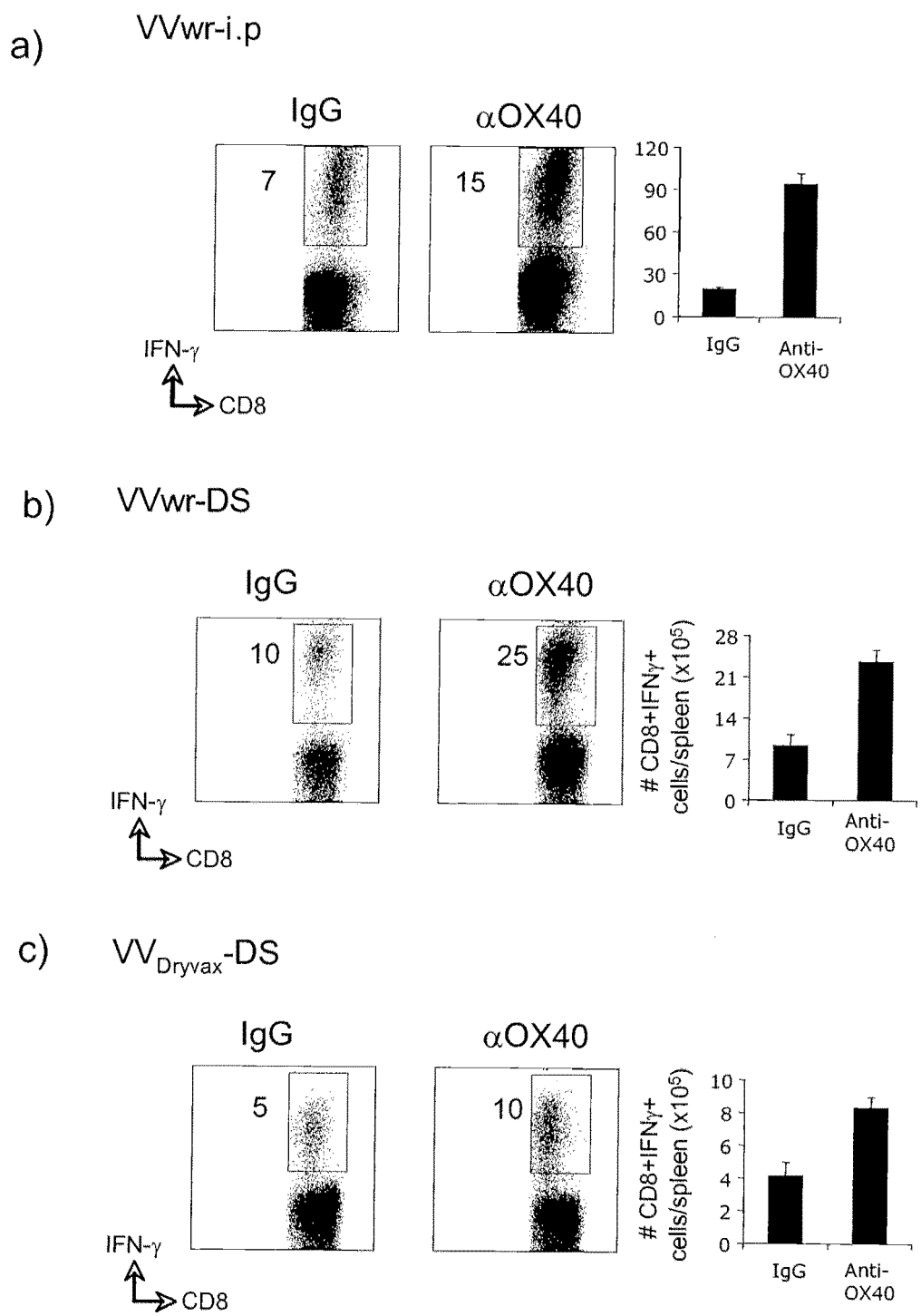
FIGS. 1A-1C show data indicating enhanced CD8 T cell responses to Vaccinia virus following anti-OX40 antibody treatment. Mice were infected with either VVwr (A and B) or $VV_{Dryvax}$ (C) through intraperitoneal (i.p, A) or dermal scarification (DS, B and C), and then treated with either anti-OX40 or rat IgG as indicated. Numbers of IFN-γ-secreting CD8 cells were determined after stimulation with B8R peptide (TSYKFESV, SEQ ID NO:1). Results are means±SEM of 4 mice/group.

In FIG. 1, Wild type C57BL/6 mice were injected with either vaccinia virus western reserve strain (VVwr, a and b; $2\times10^5$ PFU) or vaccinia virus Dryvax strain ($VV_{Dryvax}$, c; $2\times10^5$ PFU) through intraperitoneal (i.p) or dermal scarification (ds) routes, and one day later received a single dose 150 µg of either agonist anti-OX40 antibody or control rat IgG. 8 days after infection, numbers of IFN-γ-secreting CD8 cells reactive with B8R peptide (the immunodominant CD8 epitope recognized in VV) were determined by intracellular cytokine staining 5 hrs after stimulation with B8R peptide. This study demonstrates a significant enhancement of CD8 T cell priming after OX40 stimulation.

Figure 2:
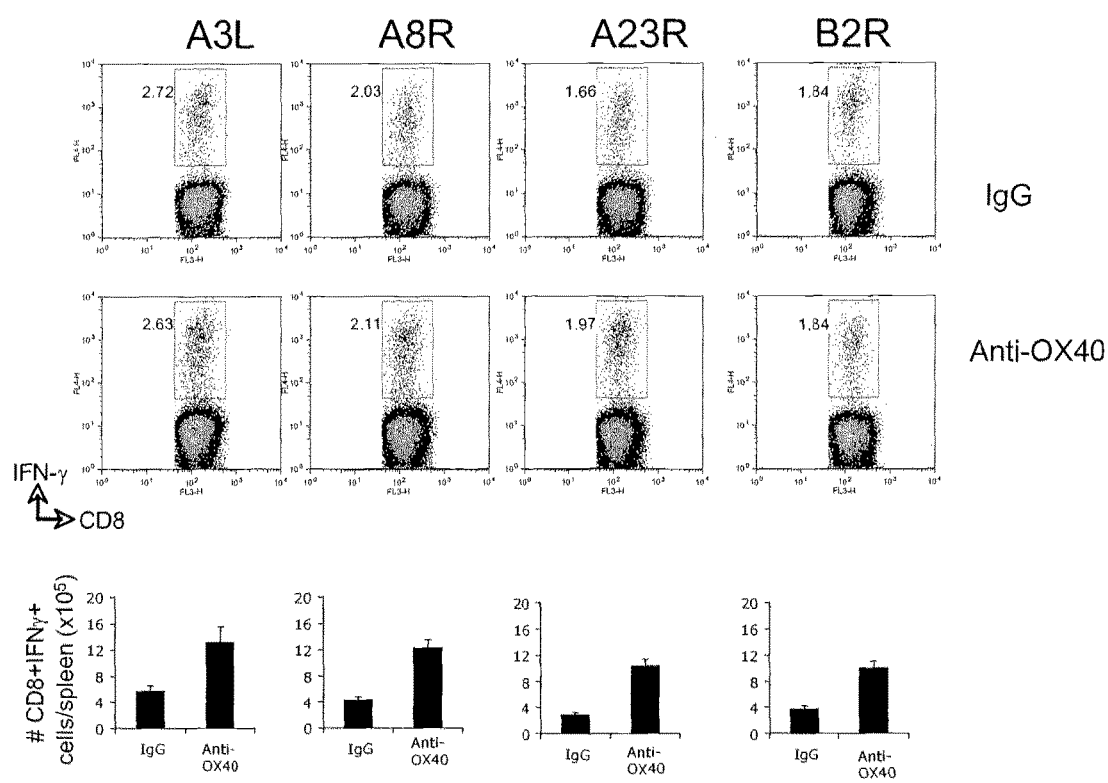
FIG. 2 shows data indicating enhanced CD8 T cell responses to Vaccinia virus following anti-OX40 antibody treatment. Mice were infected with VVw, and then treated with either anti-OX40 or rat IgG as indicated. Numbers of IFN-γ-secreting CD8 cells were determined after stimulation with A3L (KSYNYMLL, SEQ ID NO:2), A8R (ITYRFYLI, SEQ ID NO:3), A23R (IGMFNLTFI, SEQ ID NO:4), and B2R(YSQVNKRYI, SEQ ID NO:5) peptides. Results are means±SEM of 4 mice/group.

FIG. 2 illustrates a similar analyses showing that anti-OX40 also strongly promotes expansion of CD8 T cells secreting IFN-γ that recognized other more subdominant epitopes of vaccinia (A3L, A8R, A23R, B2R). In brief, wild type C57BL/6 mice were infected with vaccinia virus western reserve strain (VVwr, $2\times10^5$ PFU) through the intraperitoneal (i.p) route. One day later mice were received 150 µl of either anti-OX40 or rat IgG. 8 days after infection, numbers of IFN-γ-secreting CD8 cells were assessed by intracellular cytokine staining 5 hrs after stimulation with A3L, A8R, A23R, and B2R peptides.

Figure 3:
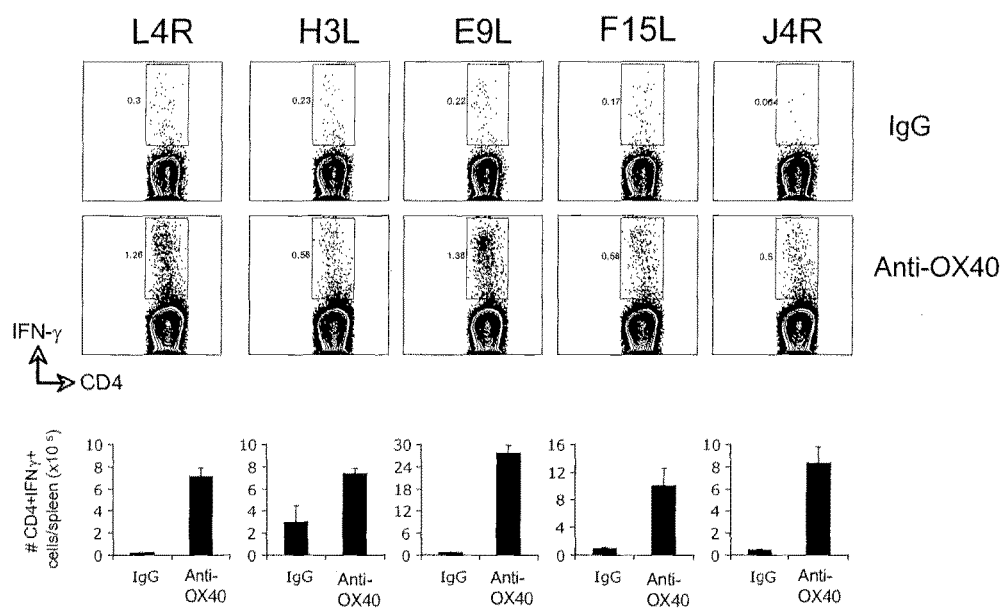
FIG. 3 shows data indicating enhanced CD4 T cell responses to Vaccinia virus following anti-OX40 antibody treatment. Mice were infected with VVwr, and then treated with either anti-OX40 or rat IgG as indicated. Numbers of IFN-γ-secreting CD4 cells were determined after stimulation with L4R (ISKYAGINILNVYSP, SEQ ID NO:6), H3L (PGVMYAFTTPLISFF, SEQ ID NO:7), E9L (PSVFIN-PISHTSYCY, SEQ ID NO:8), F15L (TPRYIPSTSISSSNI, SEQ ID NO:9) and J4R (DDDYGEPIIITSYLQ, SEQ ID NO:10) peptides. Results are means±SEM of 4 mice/group.

To examine anti-VV CD4 T cell priming, mice were again immunized with VVwr i.p. with or without treatment from anti-OX40 and the number of CD4 cells capable of secreting IFN-γ in response to defined CD4 epitopes of VV was examined. In brief, wild type C57BL/6 mice were infected with vaccinia virus western reserve strain (VVwr; $2\times10^5$ PFU) through the intraperitoneal (i.p) route. One day later mice were treated with 150 µg of either anti-OX40 or control rat IgG. 8 days after infection, numbers of IFN-γ-secreting CD4 cells were assessed by intracellular cytokine staining 5 hrs after stimulation with L4R, H3L, E9L, F15L and J4R peptides. In FIG. 3, the data show that OX40 stimulation also strongly enhanced the accumulation of anti-VV CD4 cells to all of the major epitopes of VV that are recognized by CD4 cells (L4R, H3L, E9L, F15L, J4R)

Figure 4:
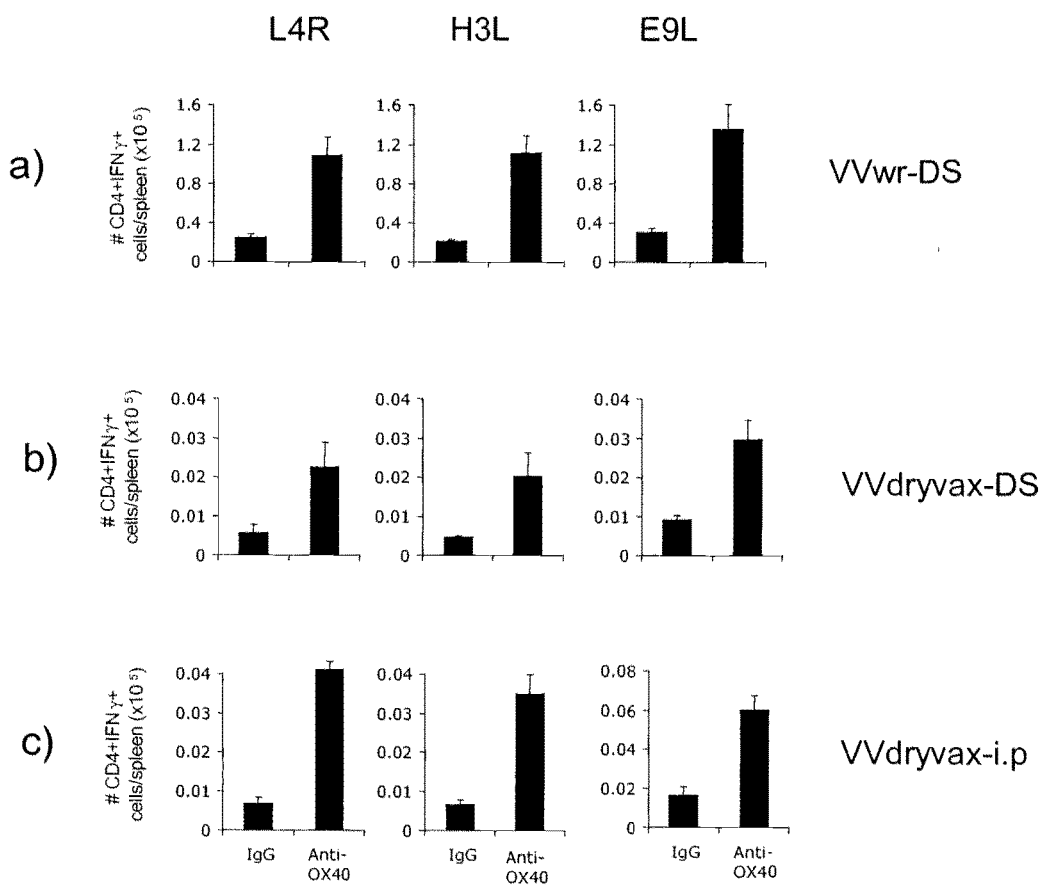
FIGS. 4A-4C show data indicating enhanced CD4 T cell responses to Vaccinia virus given by various routes following anti-OX40 antibody treatment. Mice were infected with VVwr (A) or $VV_{Dryvax}$ (B and C) via DS (A and B) or i.p (C) routes, and then treated with either anti-OX40 or rat IgG. Numbers of IFN-γ-secreting CD4 cells were determined after stimulation with L4R, H3L, and E9L peptides. Results are means SEM of 4 mice/group.

To examine if CD4 T cell priming is affected by the route of administration or strain of vaccinia virus, wild type C57BL/6 mice were infected with either vaccinia virus western reserve strain (VVwr, a; $2\times10^5$ PFU) or Dryvax ($VV_{Dryvax}$, b and c; $2\times10^5$ PFU) through dermal scarification (DS; a and b) or intraperitoneal (i.p; c) routes. One day later mice were treated with 150 µg of either anti-OX40 or control rat IgG. 8 days after infection, numbers of IFN-γ-secreting CD4 cells were assessed by intracellular cytokine staining 5 hrs after stimulation with L4R, H3L, and E9L peptides. In FIG. 4, the data show that the same result is achieved whether VVwr is given i.p. or through dermal scarification or in response to VV Dryvax.

In summary, the data in FIGS. 1 to 4 demonstrate that agonist anti-OX40 enhances priming of CD8 and CD4 T cells to whole virus immunization that recognize multiple peptide epitopes of both an attenuated virus (VVwr) and the smallpox vaccine (VV Dryvax).

Example 3

This example includes a description of data indicating that anti-OX40 agonistic antibody treatment combined with a single CD8 T cell peptide epitope of vaccinia or CD4 T cell peptide epitopes of vaccinia protect mice against lethal vaccinia virus challenge.

To determine if targeting OX40 could provide enhanced protection against VV when given prophylactically, Wild type C57BL/6 mice were immunized subcutaneously at the base of the tail with varying concentrations of the immunodominant anti-VV CD8 peptide B8R (2 µg) or B16R (2 µg) given in emulsified IFA with or without anti-OX40 treatment one day later. Control groups of mice received injections of adjuvant alone or adjuvant plus anti-OX40 mAb. 16 days later mice were exposed intranasally to VVwr ($3.5 \times 10^6$ PFU), a dose that results in lethality due to loss of body weight and other factors associated with massive lung inflammatory responses. Five days after intranasal challenge the numbers of IFN-γ-secreting CD8 cells were assessed by intracellular cytokine staining 5 hrs after stimulation with B8R peptide.

Figure 5:
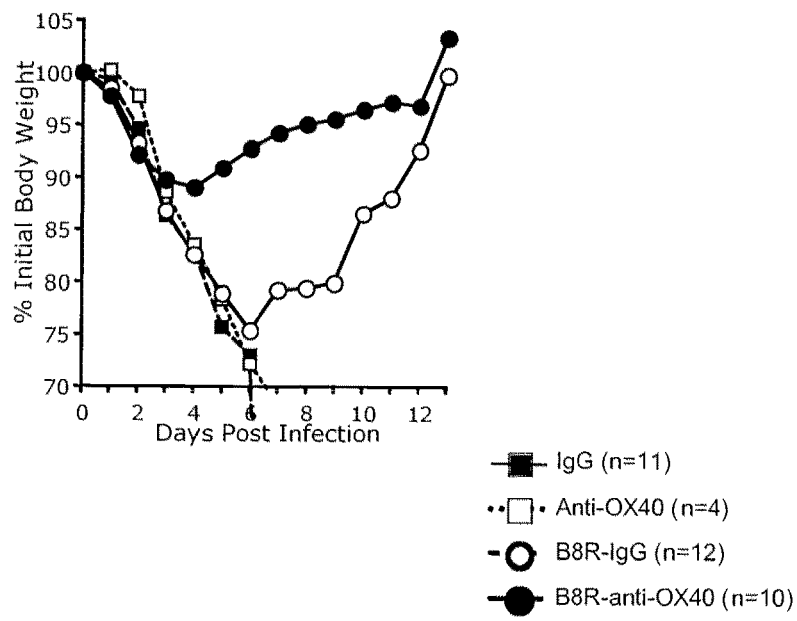
FIGS. 5A-5E show data indicating anti-OX40 agonistic antibody treatment combined with a single CD8 T cell peptide epitope of vaccinia (B8R) protects mice against lethal vaccinia virus challenge. Mice were immunized with B8R peptide (A-C) or B16R (ISVANKIYM) peptide (D-E) and one day later treated with either anti-OX40 or rat IgG. Control mice received injections of adjuvant alone or adjuvant plus anti-OX40 antibody. A) and E) Body weight after intranasal challenge with VVwr; B) and D) Survival curve after intranasal challenge with VVwr; and C) Numbers of IFN-γ-secreting CD8 cells after intranasal challenge after stimulation with B8R peptide.
Figure 5:
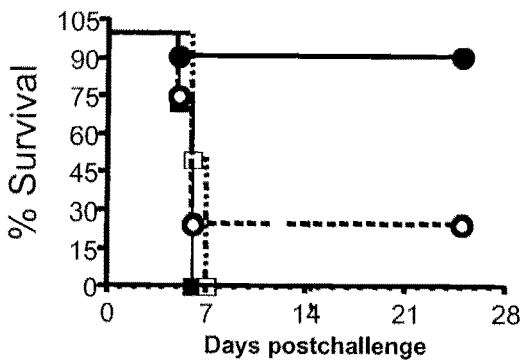
Figure 5:
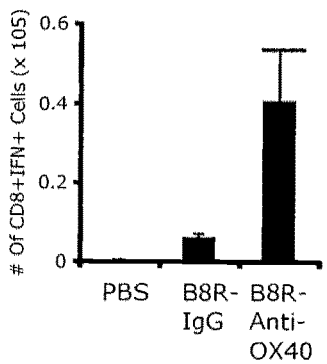
Figure 5:
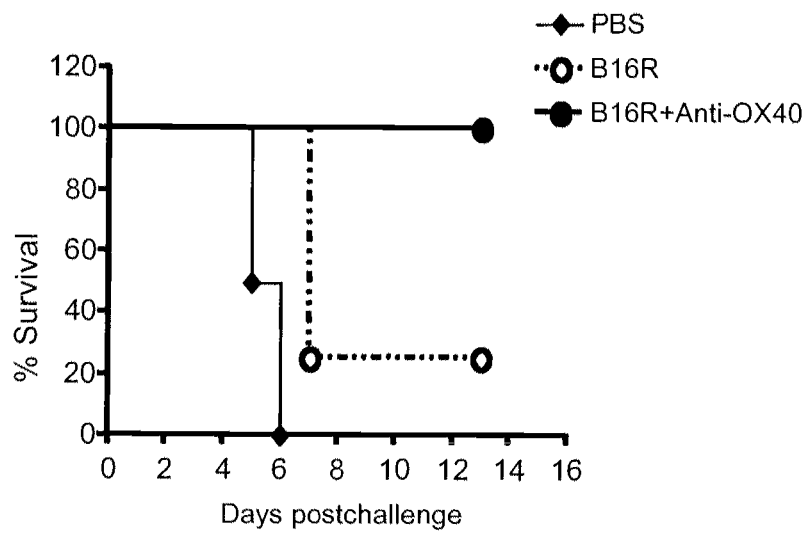
Figure 5:
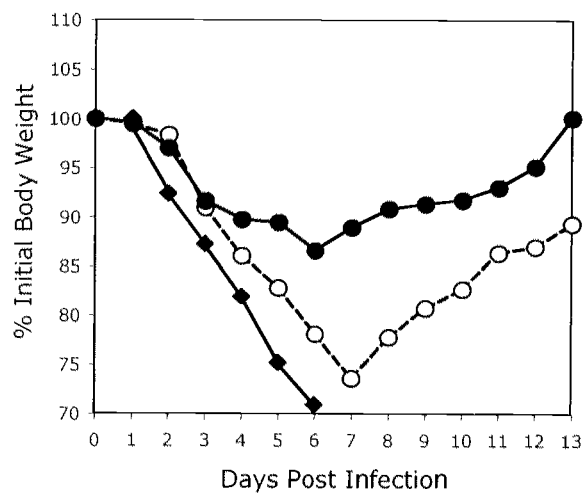

FIG. 5 illustrates A) and E) Body weight after VVwr intranasal challenge, B) and D) survival after intranasal challenge, and C) numbers of IFN-γ-secreting CD8 cells. The data show that mice immunized with B8R peptide or B16 R peptide alone were partially protected with 4 out of 12 mice surviving the challenge, whereas mice receiving anti-OX40 were completely protected from loss of body weight and 9 out of 10 mice survived, correlating with enhanced numbers of CD8 T cells accumulating in the lung following OX40 stimulation.

Figure 6:
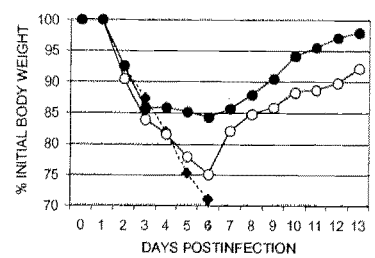
FIGS. 6A-6C show data indicating anti-OX40 agonist antibody treatment combined with single CD4 T cell peptide epitopes of vaccinia protect mice against lethal vaccinia virus challenge. Mice were immunized with A) B2R (VKD-KYMWCYSYSQVNKR, SEQ ID NO:11); B) I1L (QLVF-NSISARALKAY, SEQ ID NO:12); and C) L4R peptides, and one day later treated with either anti-OX40 or rat IgG as indicated. Control groups of mice received adjuvant alone.
Figure 6:
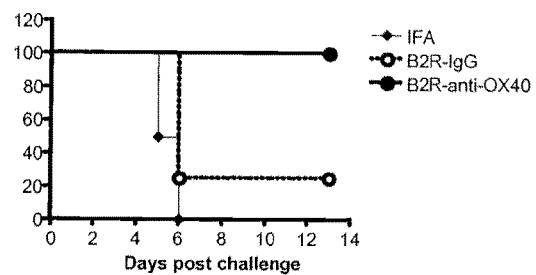
Figure 6:
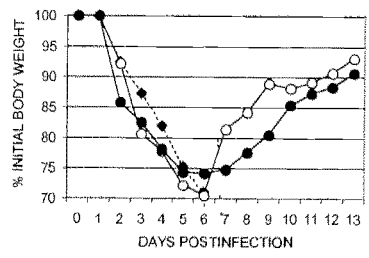
Figure 6:
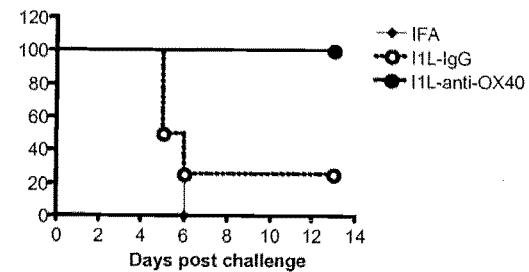
Figure 6:
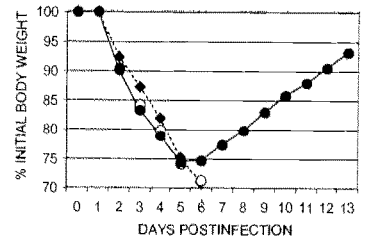
Figure 6:
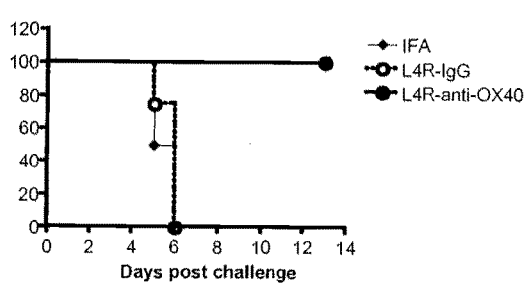

Similar data were obtained using CD4 epitopes (I1L, L4R) and B2R. In brief, wild type C57BL/6 mice were immunized subcutaneously at the base of the tail with 30µg of B2R, I1L, or L4R peptides emulsified in CFA. One day later mice were treated with 150 µg of either rat IgG or anti-OX40. Control groups of mice received injections of adjuvant alone. (Left panel) Body weight was monitored after intranasal challenge with 2×106 PFU of vaccinia virus western reserve strain (VVwr). As shown in FIG. 6, anti-OX40 combined with peptide immunization resulted in almost complete protection from lethal virus challenge. This further shows that agonist anti-OX40 promotes immunity against VV infection when combined with vaccination using defined peptide epitopes of VV.

FIGS. 7A-7B illustrates that OX40 activation inhibits MCMV replication and enhances generation of protective T cells. A) MCMV-infected mice were treated with IgG (closed bars) or anti-OX40 (open bars) and after 7 and 30 days salivary glands were assayed for infectious virus. B) (left) Numbers of CD4 T cells in the salivary glands of IgG and anti-OX40 treated mice 0, 7, 14 and 30 days post-infection. B), right) IFNγ and IL-10 expression was measured in salivary gland-derived CD4 T cells following ex-vivo stimulation with anti-CD3 and anti-CD28. Ratio of IFNγ:IL-10 producing CD4 cells, calculated as the ratio of the percentages of IFNγ expressing CD4 cells to IL-10 expressing CD4 cells.

In sum, the data demonstrate that targeting OX40 can enhance priming of both CD8 and CD4 T cells that provide protection against vaccinia virus and cytomegalovirus. Hence targeting OX40 with agonists, such as antibodies, can provide protection against smallpox, herpesviruses and other viruses. Agonist reagents to OX40 can also be combined with the current smallpox vaccine, Dryvax, to allow reduced doses of this vaccine to be used with the same efficacy as higher doses of vaccine. Moreover, OX40 agonists can be employed in combination with defined CD8 and CD4 epitopes of viruses, such as Dryvax or smallpox to immunize against smallpox or other viral infections to create a vaccine without relying on vaccinating or immunizing with whole virus.

Example 4

This example includes a description of various OX40 antibodies.

Several anti-human OX40 antibodies have been reported including mAb 315 and 131 (Imura et al, J Exp Med. 183(5):2185-95 (1996); and Ohshima et al, Blood 92(9): 3338-45 (1998)) and mAb 2G2, IF7, and ACT35 (Xie et al, Tissue Antigens. 67(4):307-17 (2006)), and mAb L106 (commercially available, BD Pharmingen). Rat anti-mouse OX40, mAb OX86 (Al-Shamkhani et al, Eur J Immunol 26:1695-1 (1996)) used in the vaccinia and CMV studies is commercially available. Antibodies that specifically bind to OX40, denoted as 112F32, 112V8, 112Y55, 112Y131, and 112Z5, which are human monoclonal anti-human OX40 antibodies (human antibodies that bind to human OX40), are described in WO 2007/062445.

What is claimed:

1. A method of inducing a CD8+ T cell response to protect a subject against poxvirus replication, comprising administering to the subject a CD8+ T cell specific poxvirus antigen and an amount of an OX40 (CD 134) agonist sufficient to induce the CD8+ T cell response of the subject, thereby protecting the subject against the poxvirus replication wherein the CD8+ T cell specific poxvirus antigen is a cell free CD8+ peptide.

2. A method of treating a subject having a viral infection caused by a poxvirus, comprising administering to the subject a CD8+ T cell specific poxvirus antigen and an amount of an OX40 agonist sufficient to enhance or augment an anti-viral CD8+ T cell response of the subject, thereby protecting the subject against the viral infection, wherein the CD8+ T cell specific poxvirus antigen is a cell free CD8+ peptide.

3. The method of claim 1, wherein the OX40 (CD134) agonist comprises an antibody.

4. The method of claim 3, wherein the antibody is mammalian, primatized, humanized or fully human.

5. The method of claim 3, wherein the antibody is monoclonal or polyclonal.

6. The method of claim 2, wherein the viral infection is acute.

7. The method of claim 1, wherein the subject is a mammal.

8. The method of claim 1, wherein the subject is a human.

9. The method of claim 1 or 2, wherein the CD8+ T cell specific poxvirus antigen comprises a vaccinia virus, *Molluscum contagiosum*, variola major or variola minor smallpox virus, cow pox, camel pox, sheep pox, or monkey pox antigen.

10. The method of claim 9, wherein the CD8+ T cell specific poxvirus antigen is a vaccinia virus antigen selected from a B8R, A3L, A8R, A23R or B2R antigen.

11. The method of claim 2, wherein the poxvirus comprises a vaccinia virus, *Molluscum contagiosum*, variola major or variola minor smallpox virus, cow pox, camel pox, sheep pox, or monkey pox.

12. The method of claim 1, wherein the method reduces the amount of a poxvirus protein.

13. The method of claim 1 or 2, wherein the OX40 (CD134) agonist is administered prior to, substantially contemporaneously with or following administration of the CD8+ T cell specific poxvirus antigen.

14. The method of claim 1 or 2, wherein the OX40 (CD 134) agonist is administered prior to, substantially contemporaneously with or following exposure to or infection of the subject with the poxvirus.

15. A method of inducing an antiviral CD8+ T cell response in a subject with a viral infection caused by a poxvirus to protect the subject against poxvirus replication, comprising administering to the subject a CD8+ T cell specific poxvirus antigen and an amount of OX40 (CD134) agonist sufficient to induce the antiviral CD8+ T cell response in the subject to protect the subject against poxvirus replication, wherein the CD8+ T cell specific poxvirus antigen is a cell free CD8+ peptide and wherein the CD8+ T cell specific poxvirus antigen is administered prior to administration of the OX40(CD134) agonist to the subject.

16. The method of claim 1, wherein the CD8+ T cell specific poxvirus antigen consists of a class I restricted CD8+ T cell peptide epitope.

\* \* \* \* \*

UNITED STATES PATENT AND TRADEMARK OFFICE
CERTIFICATE OF CORRECTION

PATENT NO. : 10,106,619 B2
APPLICATION NO. : 11/867621
DATED : October 23, 2018
INVENTOR(S) : Michael Croft et al.

Page 1 of 1

It is certified that error appears in the above-identified patent and that said Letters Patent is hereby corrected as shown below:

In Column 16, Line 49:
Replace "pol protein p17, p17"
With --pol protein p7, p17--

In Column 21, Line 9:
Replace "TransVer-S al"
With --TransVer-Sal--

In Column 26, Line 32:
Replace "methyl guanine"
With --methylguanine--

In Column 29, Lines 56-57:
Replace "manufacture's"
With --manufacturer's--

In Column 30, Lines 26-27:
Replace "mice were received 150 microliters"
With --mice were received 150 micrograms--

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 15

<210> SEQ ID NO 1
<211> LENGTH: 8
<212> TYPE: PRT
<213> ORGANISM: Pox viridae

<400> SEQUENCE: 1

Thr Ser Tyr Lys Phe Glu Ser Val
1               5

<210> SEQ ID NO 2
<211> LENGTH: 8
<212> TYPE: PRT
<213> ORGANISM: Pox viridae

<400> SEQUENCE: 2

Lys Ser Tyr Asn Tyr Met Leu Leu
1               5
```

<210> SEQ ID NO 3
<211> LENGTH: 8
<212> TYPE: PRT
<213> ORGANISM: Pox viridae

<400> SEQUENCE: 3

Ile Thr Tyr Arg Phe Tyr Leu Ile
1               5

<210> SEQ ID NO 4
<211> LENGTH: 9
<212> TYPE: PRT
<213> ORGANISM: Pox viridae

<400> SEQUENCE: 4

Ile Gly Met Phe Asn Leu Thr Phe Ile
1               5

<210> SEQ ID NO 5
<211> LENGTH: 9
<212> TYPE: PRT
<213> ORGANISM: Pox viridae

<400> SEQUENCE: 5

Tyr Ser Gln Val Asn Lys Arg Tyr Ile
1               5

<210> SEQ ID NO 6
<211> LENGTH: 15
<212> TYPE: PRT
<213> ORGANISM: Pox viridae

<400> SEQUENCE: 6

Ile Ser Lys Tyr Ala Gly Ile Asn Ile Leu Asn Val Tyr Ser Pro
1               5                   10                  15

<210> SEQ ID NO 7
<211> LENGTH: 15
<212> TYPE: PRT
<213> ORGANISM: Pox viridae

<400> SEQUENCE: 7

Pro Gly Val Met Tyr Ala Phe Thr Thr Pro Leu Ile Ser Phe Phe
1               5                   10                  15

<210> SEQ ID NO 8
<211> LENGTH: 15
<212> TYPE: PRT
<213> ORGANISM: Pox viridae

<400> SEQUENCE: 8

Pro Ser Val Phe Ile Asn Pro Ile Ser His Thr Ser Tyr Cys Tyr
1               5                   10                  15

<210> SEQ ID NO 9
<211> LENGTH: 15
<212> TYPE: PRT
<213> ORGANISM: Pox viridae

<400> SEQUENCE: 9

Thr Pro Arg Tyr Ile Pro Ser Thr Ser Ile Ser Ser Ser Asn Ile
1               5                   10                  15

-continued

```
<210> SEQ ID NO 10
<211> LENGTH: 15
<212> TYPE: PRT
<213> ORGANISM: Pox viridae

<400> SEQUENCE: 10

Asp Asp Asp Tyr Gly Glu Pro Ile Ile Ile Thr Ser Tyr Leu Gln
1               5                   10                  15

<210> SEQ ID NO 11
<211> LENGTH: 17
<212> TYPE: PRT
<213> ORGANISM: Pox viridae

<400> SEQUENCE: 11

Val Lys Asp Lys Tyr Met Trp Cys Tyr Ser Tyr Ser Gln Val Asn Lys
1               5                   10                  15

Arg

```
                195                 200                 205
Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 14
<211> LENGTH: 203
<212> TYPE: PRT
<213> ORGANISM: Homo sapiens

<400> SEQUENCE: 14

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser
        195                 200

<210> SEQ ID NO 15
<211> LENGTH: 183
<212> TYPE: PRT
<213> ORGANISM: Homo sapiens

<400> SEQUENCE: 15

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
```

-continued

```
            35                  40                  45
Ala Leu Gln Val Ser His Arg Tyr Pro Arg Ile Gln Ser Ile Lys Val
         50                  55                  60

Gln Phe Thr Glu Tyr Lys Lys Glu Lys Gly Phe Ile Leu Thr Ser Gln
 65                  70                  75                  80

Lys Glu Asp Glu Ile Met Lys Val Gln Asn Asn Ser Val Ile Ile Asn
                 85                  90                  95

Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Glu Pro Leu Phe Gln
             115                 120                 125

Leu Lys Lys Val Arg Ser Val Asn Ser Leu Met Val Ala Ser Leu Thr
         130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
             180
```